United States Patent
Porowski et al.

(10) Patent No.: US 12,310,433 B2
(45) Date of Patent: May 27, 2025

(54) COMPACTABLE SURFACE COVERING MEMBER AND METHOD FOR COMPACTING THE SAME

(71) Applicant: GoGown, LLC, Raleigh, NC (US)

(72) Inventors: Virginia Porowski, Wake Forest, NC (US); Nicholas William Medendorp, Jr., Carmel, IN (US)

(73) Assignee: GoGown, LLC, Raleigh, NC (US)

( * ) Notice: Subject to any disclaimer, the term of this patent is extended or adjusted under 35 U.S.C. 154(b) by 0 days.

(21) Appl. No.: 18/432,745

(22) Filed: Feb. 5, 2024

(65) Prior Publication Data

US 2025/0017295 A1    Jan. 16, 2025

Related U.S. Application Data

(60) Provisional application No. 63/621,573, filed on Jan. 16, 2024, provisional application No. 63/525,792, filed on Jul. 10, 2023.

(51) Int. Cl.
*A61B 46/00* (2016.01)
*A41D 13/12* (2006.01)

(52) U.S. Cl.
CPC .............. *A41D 13/12* (2013.01); *A61B 46/00* (2016.02)

(58) Field of Classification Search
CPC ........... A61B 2046/201–236; A61B 46/00–40; A47G 11/003; A47G 11/004;
(Continued)

(56) References Cited

U.S. PATENT DOCUMENTS

| 2,143,931 | A | 1/1939 | Aronson |
| 2,146,243 | A | 2/1939 | Aug |

(Continued)

FOREIGN PATENT DOCUMENTS

| CN | 105662690 B | 6/2016 |
| WO | 82001119 A1 | 4/1982 |
| WO | 2020131172 A1 | 6/2020 |

OTHER PUBLICATIONS

Author Unknown, "AAMI Level Standards for Gowns," munglobal.com/resources/aami-level-standards-for-gowns/, accessed Mar. 11, 2024, Mun Global, 4 pages.
(Continued)

*Primary Examiner* — Adam Baker
(74) *Attorney, Agent, or Firm* — Withrow + Terranova, PLLC; Vincent K. Gustafson

(57) ABSTRACT

A surface covering member includes a wrapper panel and pliable sheet material with at least one liquid-penetration-resistant layer. The wrapper panel may at least partially envelop the pliable sheet material when the pliable sheet material is compacted. At least one accordion fold may be provided along one or more peripheral edges, optionally with the wrapper panel forming a pouch. First and second wrapper panels may be arranged at first and second positions of the pliable sheet material. A wrapper panel may be a continuous extension of the pliable sheet material, and at least one selectively deployable adhesive tab at a peripheral edge of the wrapper panel affixes the wrapper panel against the pliable sheet material when the surface covering member is in a non-compacted state, and at least partially envelops the pliable sheet material when it is compacted by rolling and/or folding to maintain the compacted pliable sheet material in the at least partially enveloped state.

18 Claims, 11 Drawing Sheets

(58) Field of Classification Search
CPC ...... A47G 11/007; A47G 9/0246; A47G 9/08; A47G 9/06; A47G 9/062; A47G 11/006; A47G 11/008; A61F 5/485; A61F 13/15; A61F 13/505–58; A61F 5/48; A47C 27/002–008; A47C 31/10–116; B65F 1/0006; A41D 13/12–129

USPC .......................... 108/90; 128/849; 5/482, 485

See application file for complete search history.

(56) References Cited

U.S. PATENT DOCUMENTS

| | | | |
|---|---|---|---|
| 2,292,347 | A | 8/1942 | Bailey |
| 2,324,722 | A | 7/1943 | Papierniak |
| 2,325,494 | A | 7/1943 | Fayer |
| 2,513,074 | A | 7/1948 | Wolfe |
| 2,668,294 | A | 2/1954 | Gilpin |
| 2,825,902 | A | 3/1958 | Breier |
| 2,959,789 | A | 11/1960 | Mills et al. |
| 2,971,198 | A | 2/1961 | Tomich |
| 3,085,254 | A | 4/1963 | Cutler |
| 3,451,062 | A | 6/1969 | Bradley |
| 3,604,423 | A * | 9/1971 | Fraser ...................... A61F 13/56 604/385.13 |
| 3,721,999 | A | 3/1973 | Goya et al. |
| 3,745,587 | A | 7/1973 | Bradley |
| 3,865,303 | A | 2/1975 | Korn |
| 4,051,845 | A | 10/1977 | Collins |
| 4,064,562 | A | 12/1977 | Kenny |
| 4,404,689 | A | 9/1983 | DeWan |
| 4,414,968 | A * | 11/1983 | Amin ...................... A61B 46/30 128/853 |
| 4,476,587 | A | 10/1984 | Itoi |
| D277,048 | S | 1/1985 | Peyser |
| D277,049 | S | 1/1985 | Peyser |
| 4,542,050 | A | 9/1985 | Gallant |
| 4,608,719 | A | 9/1986 | Lunt |
| 4,700,409 | A | 10/1987 | De Lott |
| 4,705,171 | A | 11/1987 | Eldridge |
| 4,783,854 | A | 11/1988 | Bjorklund |
| 4,819,275 | A | 4/1989 | Lunt |
| 4,845,779 | A | 7/1989 | Wheeler et al. |
| 4,944,042 | A | 7/1990 | DeWan |
| 5,010,592 | A | 4/1991 | Skiles, Jr. |
| 5,048,123 | A | 9/1991 | Monson |
| 5,345,946 | A | 9/1994 | Butterworth et al. |
| 5,361,781 | A | 11/1994 | Antonini |
| 5,410,758 | A | 5/1995 | Dupont et al. |
| 5,476,456 | A * | 12/1995 | Rankin ................. A47C 27/005 5/500 |
| 5,483,701 | A | 1/1996 | Ferreyros |
| 5,584,077 | A | 12/1996 | Thrift |
| 5,628,067 | A | 5/1997 | Meyer et al. |
| 5,699,560 | A | 12/1997 | Greenberg |
| 6,179,819 | B1 | 1/2001 | Haswell |
| 6,213,124 | B1 | 4/2001 | Butterworth |
| 6,725,864 | B2 | 4/2004 | Ewonce et al. |
| 6,742,189 | B2 | 6/2004 | Bennett |
| 6,817,031 | B1 | 11/2004 | Gravlin |
| 6,874,505 | B1 | 4/2005 | Fenwick et al. |
| 7,143,450 | B2 | 12/2006 | Green, III |
| 7,246,382 | B2 | 7/2007 | Plut et al. |
| 7,269,855 | B2 | 9/2007 | LaRocco |
| 7,302,711 | B1 | 12/2007 | Tanenbaum |
| 7,395,555 | B2 | 7/2008 | Aldridge et al. |
| 7,544,186 | B2 | 6/2009 | Davis et al. |
| 7,867,208 | B2 | 1/2011 | Samuelsson et al. |
| 8,056,146 | B2 | 11/2011 | Porowski |
| 8,216,200 | B2 | 7/2012 | Meetz et al. |
| 8,230,519 | B2 | 7/2012 | Porowski |
| 11,076,648 | B2 | 8/2021 | Benson et al. |
| 2004/0028853 | A1 * | 2/2004 | Jackson ................. B65F 1/0006 428/35.5 |
| 2005/0071920 | A1 * | 4/2005 | Higashi .................. A47G 9/062 383/4 |
| 2005/0223471 | A1 * | 10/2005 | Griesbach, III et al. |
| 2005/0229937 | A1 * | 10/2005 | Salvaggio .............. A61B 50/13 128/849 |
| 2006/0219249 | A1 | 10/2006 | Czajka et al. |
| 2009/0031474 | A1 | 2/2009 | Komorowski |
| 2009/0094729 | A1 | 4/2009 | Lin et al. |
| 2010/0220941 | A1 | 9/2010 | Chen |
| 2011/0023210 | A1 * | 2/2011 | Porowski ........... A41D 13/1209 2/114 |
| 2011/0024485 | A1 | 2/2011 | Porowski |
| 2011/0107494 | A1 * | 5/2011 | Haines ................... A61B 5/411 2/48 |
| 2011/0174318 | A1 * | 7/2011 | Reyes .................... A61B 50/30 128/852 |
| 2013/0040099 | A1 | 2/2013 | Prewett |
| 2013/0131617 | A1 | 5/2013 | Kovensky |
| 2017/0325523 | A1 * | 11/2017 | Stewart ................ A41D 13/129 |
| 2019/0297967 | A1 | 10/2019 | Buffalini |
| 2020/0093298 | A1 * | 3/2020 | Jones .................. A47G 11/003 |
| 2020/0397164 | A1 | 12/2020 | Williams |
| 2022/0168060 | A1 | 6/2022 | Akahoshi |

OTHER PUBLICATIONS

Author Unknown, "Cesarean Section Surgical Drape with Pouch," Product Specification, punchout.medline.com/product/Cesarean-Section-Surgical-Drape-with-Pouch/Obstetrics/Gynecology-Drapes/Z05-PF07161, accessed Mar. 11, 2024, Medline Industries, LP, 2 pages.

Author Unknown, "Considerations for Selecting Protective Clothing used in Healthcare for Protection against Microorganisms in Blood and Body Fluids," The National Personal Protective Technology Laboratory, cdc.gov/niosh/npptl/topics/protectiveclothing/#references, last reviewed Apr. 9, 2020, Centers for Disease Control, 14 pages.

Author Unknown, "Drawstring Pad, 39', Dark Blue Polyethylene Liner with Absorbent Center Strip," Product Specification, Item No. 1220-1801, welmed.us/surgical-solutions/surgical-drapes/flat-drapes/non-sterile/drawstring-pad-39-dark-blue-polyethylene-liner-with-absorbent-center-strip/, accessed Mar. 11, 2024, Welmed, Inc., Chicago, Illinois, 5 pages.

Author Unknown, "G-Force Series: Stretcher Sheets," Product Specification, www.life-assist.com/products/details/1761/taylor-surefit-g-force-fitted-sheets/, accessed Mar. 11, 2024, Taylor Healthcare Products, Inc., Spring, Texas, 1 page.

Author Unknown, "Liquid barrier performance and classification of protective apparel and drapes intended for use in health care facilities," Ansi/Aami PB70—Class 3, cdc.gov/PPEInfo/Standards/Info/ANSI/AAMIPB70Class3, last updated Sep. 29, 2023, Centers for Disease Control, 5 pages.

Author Unknown, "Tri-Layer Fitted Sheet with Hood, 30in×72in," Product Specification, boundtree.com/patient-handling/stretcher-sheets/tri-layer-fitted-sheet-with-hood-30in-x-72in/p/3271-90003, accessed Mar. 11, 2024, Allcare Inc, 3 pages.

First Office Action for Chinese Patent Application No. 201080043325.8, mailed Dec. 4, 2013, 21 pages.

Extended European Search Report for European Patent Application No. 10804879.4, mailed Apr. 23, 2015, 7 pages.

Intention to Grant for European Patent Application No. 10804879.4, mailed Mar. 22, 2016, 6 pages.

International Search Report and Written Opinion for International Patent Application No. PCT/US10/41910, mailed Oct. 18, 2010, 8 pages.

Non-Final Office Action for U.S. Appl. No. 12/533,383, mailed Mar. 18, 2011, 5 pages.

Notice of Allowance for U.S. Appl. No. 12/533,383, mailed Sep. 15, 2011, 7 pages.

Non-Final Office Action for U.S. Appl. No. 12/707,709, mailed Oct. 4, 2011, 6 pages.

Non-Final Office Action for U.S. Appl. No. 13/238,848, mailed Mar. 14, 2012, 8 pages.

Non-Final Office Action for U.S. Appl. No. 18/436,529, mailed Jul. 3, 2024, 17 pages.

(56) References Cited

OTHER PUBLICATIONS

Final Office Action for U.S. Appl. No. 18/436,529, mailed Sep. 13, 2024, 17 pages.
Invitation to Pay Additional Fees for International Patent Application No. PCT/US2024/035374, mailed Aug. 28, 2024, 2 pages.
International Search Report and Written Opinion for International Patent Application No. PCT/US2024/035374, mailed Oct. 25, 2024, 17 pages.
Applicant-Initiated Interview Summary for U.S. Appl. No. 18/436,529, mailed Nov. 12, 2024, 17 pages.

* cited by examiner

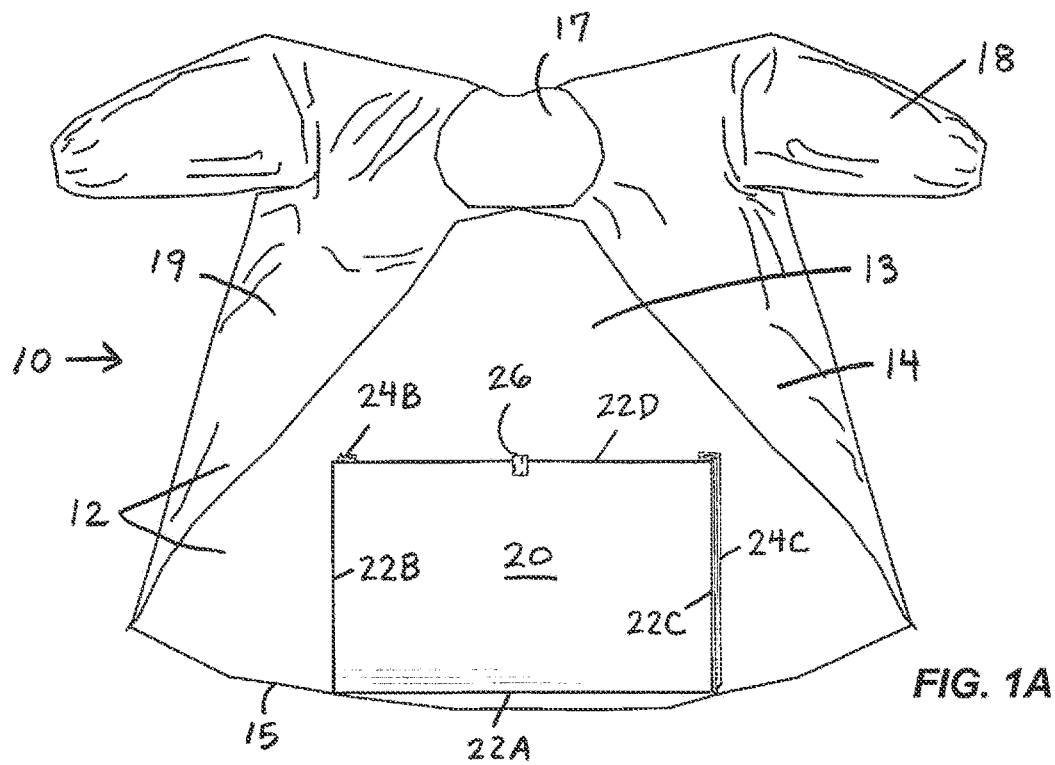
FIG. 1A
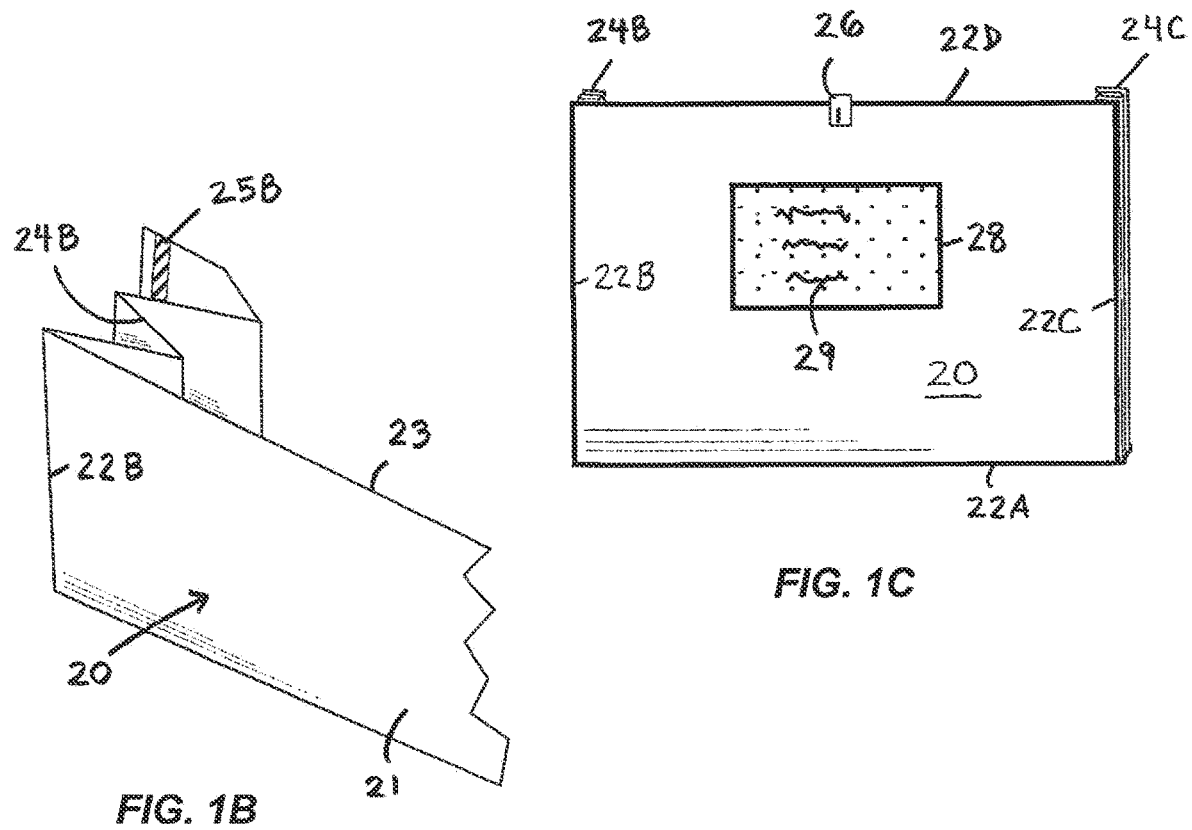
FIG. 1B
FIG. 1C

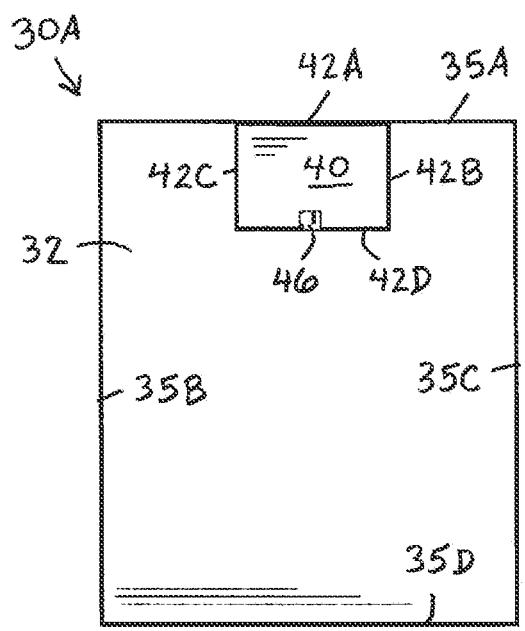
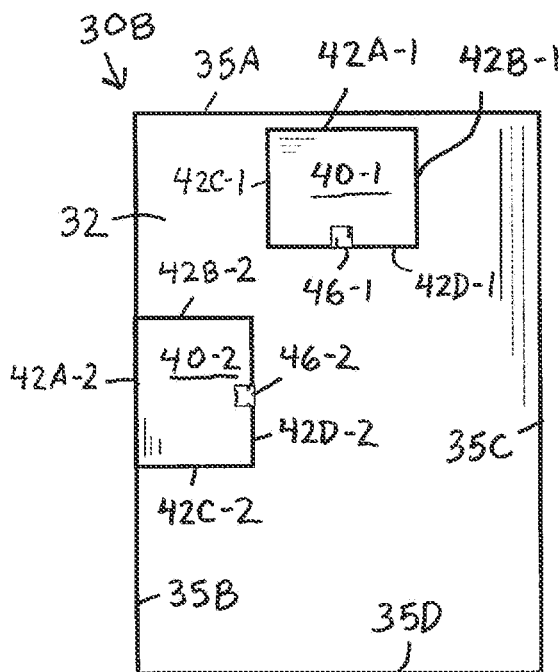
FIG. 2A
FIG. 2B
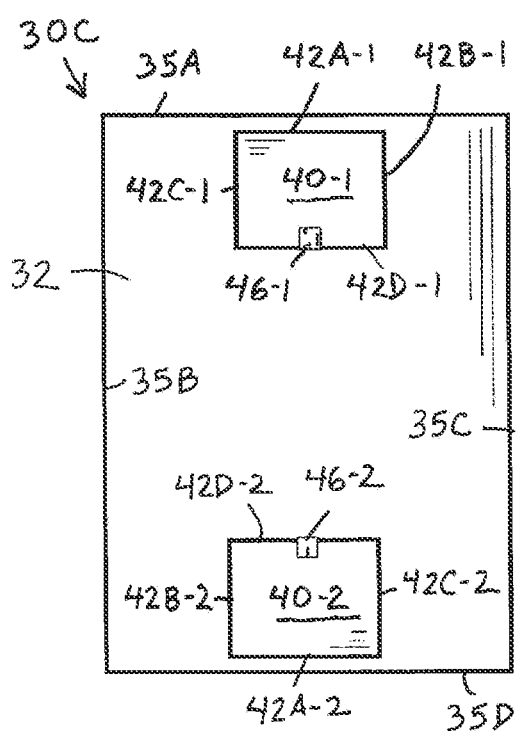
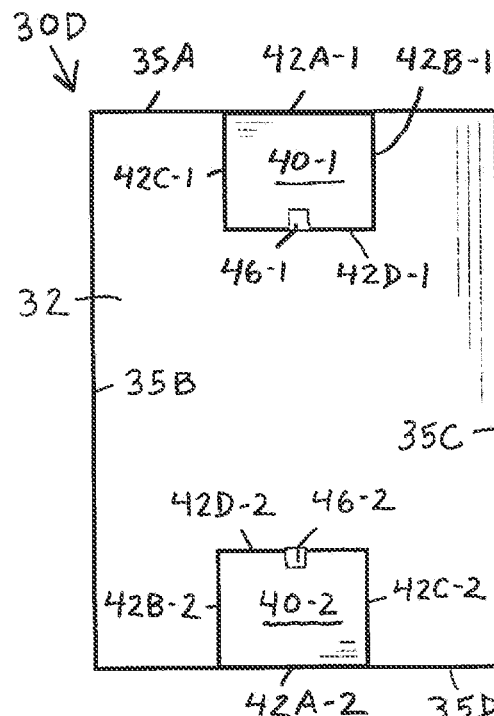
FIG. 2C
FIG. 2D

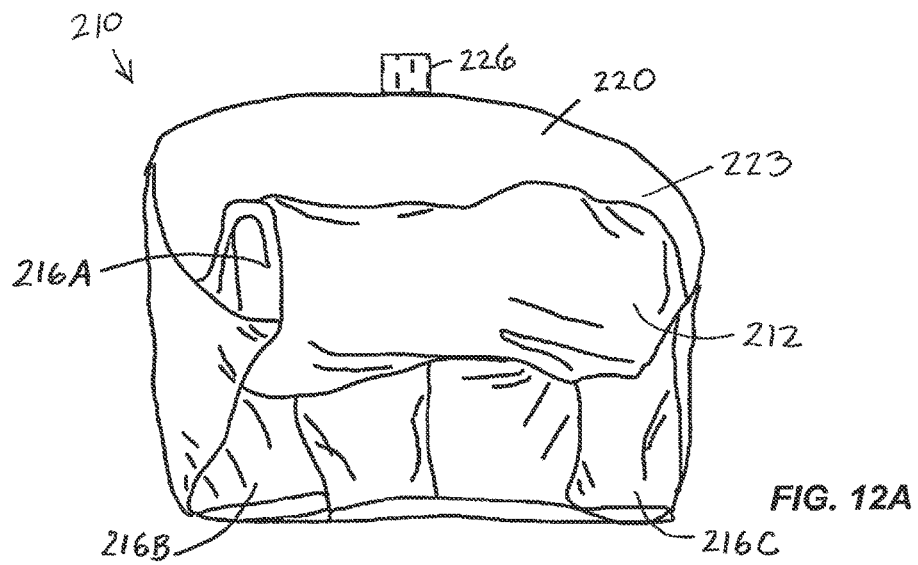
FIG. 12A
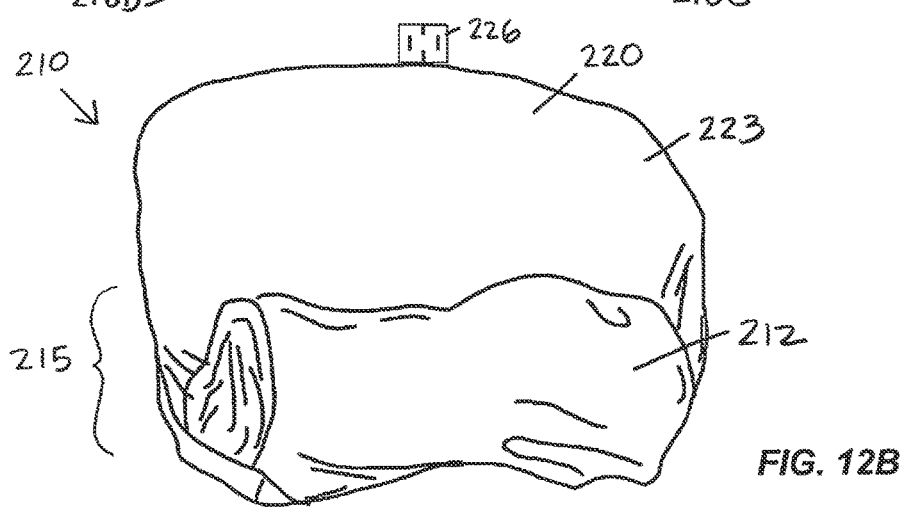
FIG. 12B
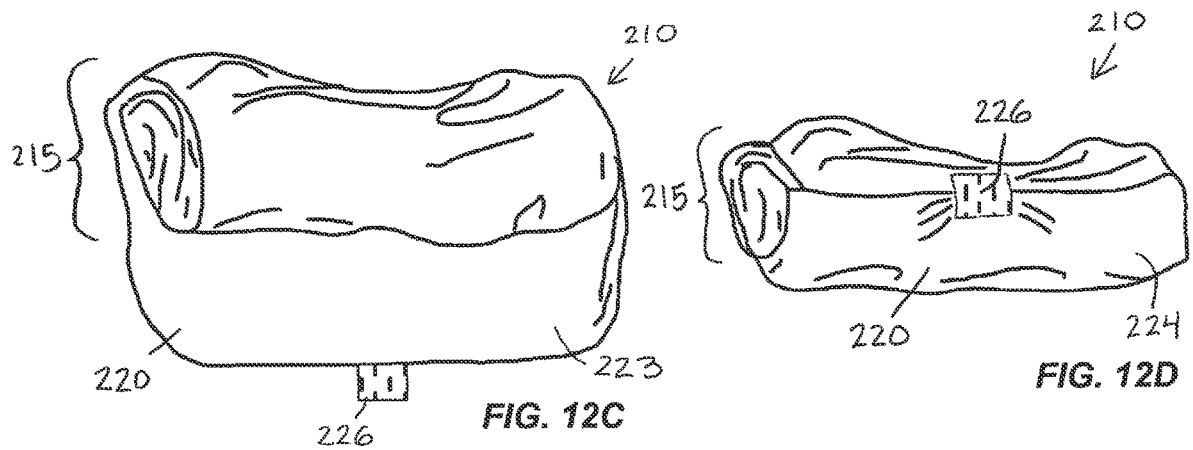
FIG. 12C
FIG. 12D

COMPACTABLE SURFACE COVERING MEMBER AND METHOD FOR COMPACTING THE SAME

CROSS-REFERENCE TO RELATED APPLICATIONS

This application claims priority to each of U.S. Provisional Patent Application No. 63/621,573 filed on Jan. 16, 2024 and U.S. Provisional Patent Application No. 63/525,792 filed on Jul. 10, 2023, wherein the entire disclosures of the foregoing applications are hereby incorporated by reference herein.

TECHNICAL FIELD

Subject matter herein relates generally to surface covering members providing liquid penetration resistance, including but not limited to wearable protective garments, healthcare and equipment drapes, bedding covers, stretcher covers, seating covers, tarpaulins, absorbent mats, and the like.

BACKGROUND

Healthcare workers and healthcare patients can be exposed to biological fluids that are capable of transmitting diseases that can pose significant risks to life and health. Various types of conventional protective garments, healthcare drapes, equipment drapes, bedding covers, stretcher covers, seating covers, tarpaulins, absorbent mats, and the like (which may be collectively referred to herein as "surface covering members") are used to cover skin surfaces and other surfaces to reduce exposure to biological fluids and to permit surfaces to be readily cleaned. Conventional surface covering members are typically disposed of after each use to minimize risk of cross-contamination.

Potential challenges associated with conventional surface covering members include safely disposing of them after use and avoiding generation of excessive waste volumes. Healthcare workers may have little guidance or training in safely compacting surface covering members. Though it would be desirable to compact surface covering members while avoiding spillage and outward exposure of biological liquids, healthcare workers may have little guidance or training in such steps. Merely stuffing contaminated surface covering members into waste disposal bins leads to inefficient disposal bin utilization, necessitating more frequent bin emptying and thereby increasing labor and healthcare costs. It would be desirable to provide improved surface covering member that address these and other limitations associated with conventional surface covering members.

SUMMARY

A surface covering member includes a pliable sheet material and a wrapper panel, the pliable sheet material including at least one liquid-penetration-resistant layer. The wrapper panel may be used to at least partially envelop the pliable sheet material when the pliable sheet material is compacted. The wrapper panel may include at least one accordion fold along one or more peripheral edges in certain embodiments, with the wrapper panel forming a pouch in certain embodiments. In certain embodiments, first and second wrapper panels may be arranged at first and second positions of the pliable sheet material. In certain embodiments, a wrapper panel may comprise a continuous extension of the pliable sheet material, and at least one selectively deployable adhesive tab positioned at a peripheral edge of the wrapper panel is configured to affix the peripheral edge against a portion of the pliable sheet material when the surface covering member is in a non-compacted state, and is configured to at least partially envelop the pliable sheet material when the pliable sheet material is compacted by one or more of rolling and folding and maintain the compacted pliable sheet material in the at least partially enveloped state.

In one aspect, the disclosure relates to a surface covering member that includes a pliable sheet material and a wrapper panel. The pliable sheet material includes at least one liquid-penetration-resistant layer, and the wrapper panel is engaged along one or more peripheral edges of the wrapper panel to the pliable sheet material. The wrapper panel includes at least one accordion fold along the one or more peripheral edges, and the wrapper panel is configured to at least partially envelop the pliable sheet material when the pliable sheet material is compacted by rolling, folding, or stuffing.

In certain embodiments, the wrapper panel comprises a continuous extension of the pliable sheet material along a first peripheral edge of the wrapper panel.

In certain embodiments, the wrapper panel is affixed to the pliable sheet material with one or more seams at second and third peripheral edges of the wrapper panel.

In certain embodiments, the wrapper panel is affixed along the one or more peripheral edges to the pliable sheet material with one or more seams, wherein the one or more seams may comprise one or more of adhesive seams, heat-welded seams, ultrasonically-welded seams, or sewn seams.

In certain embodiments, the wrapper panel forms a pouch having a pouch opening.

In certain embodiments, the surface covering member further comprises a closing member joined to one or more of the wrapper panel and the pliable sheet material, the closing member being configured to maintain the wrapper panel and the pliable sheet material in a bundled state with the compacted pliable sheet being at least partially enveloped by the wrapper panel.

In certain embodiments, the closing member comprises at least one of an adhesive surface, a portion of a hook-and-loop fastener, and one or more elongated ties extending from one or more of the wrapper panel and the pliable sheet material.

In certain embodiments, one or more of the wrapper panel and the pliable sheet material comprises a perforated region configured to form one or more elongated ties to serve as at least one closing member.

In certain embodiments, the at least one liquid-penetration-resistant layer is characterized by water impact resistance of no greater than 4.5 g when subjected to an American Association of Textile Chemists and Colorists 42 Impact Penetration test.

In certain embodiments, the pliable sheet material comprises one or more adhesive strips on the pliable sheet material and configured to permit the surface covering member to be adhered to a surface to be covered by the surface covering member.

In certain embodiments, the surface covering member comprises printed indicia on at least one of the wrapper panel and the pliable sheet, the printed indicia including instructions for use of the surface covering member to assist a user in at least partially enveloping the pliable sheet material with the wrapper panel when the pliable sheet material is compacted by rolling, folding, or stuffing.

In certain embodiments, at least a portion of the wrapper panel comprises at least one functional additive selected from the group consisting of antimicrobial agents and scented agents.

In certain embodiments, the surface covering member is embodied in a wearable protective garment configured to be worn by a human user, or is embodied in a disposable healthcare drape, a disposable healthcare equipment cover, or a disposable equipment drape, or is embodied in one of the following disposable items: a flat or fitted bedding cover, a flat or fitted stretcher cover, a blanket, a seating surface cover, a tarpaulin, and absorbent pad, or an absorbent mat.

In another aspect, the disclosure relates to a surface covering member that includes a pliable sheet material, a first wrapper panel, and a second wrapper panel. The pliable sheet material includes at least one liquid-penetration-resistant layer. The first wrapper panel is engaged along one or more peripheral edges of the first wrapper panel to the pliable sheet material to form a first pouch at a first position on the pliable sheet material, the first pouch having a first pouch opening. The second wrapper panel is engaged along one or more peripheral edges of the second wrapper panel to the pliable sheet material to form a second pouch at a second position on the pliable sheet material, the second pouch having a second pouch opening. Each of the first pouch and the second pouch is separately configured to at least partially envelop the pliable sheet when the pliable sheet is compacted by rolling, folding, or stuffing.

In certain embodiments, the first position is proximate to a first edge of the pliable sheet material, the second position is proximate to a second edge of the pliable sheet material.

In certain embodiments, the first edge of the pliable sheet material opposes the second edge of the pliable sheet material.

In certain embodiments, the first wrapper panel comprises at least one first accordion fold extending inward from the one or more first peripheral edges to permit expansion of a volume of the first pouch, and the second wrapper panel comprises at least one second accordion fold extending inward from the one or more second peripheral edges to permit expansion of a volume of the second pouch.

In certain embodiments, the first wrapper panel comprises a continuous extension of the pliable sheet material along a first peripheral edge of the first wrapper panel, and the second wrapper panel comprises a continuous extension of the pliable sheet material along a first peripheral edge of the second wrapper panel.

In certain embodiments, the first wrapper panel is affixed to the pliable sheet material with one or more first seams at second and third peripheral edges of the first wrapper panel, and the second wrapper panel is affixed to the pliable sheet material with one or more second seams at second and third peripheral edges of the second wrapper panel.

In certain embodiments, the first wrapper panel is affixed along the one or more first peripheral edges to the pliable sheet material with one or more first seams, and the second wrapper panel is affixed along the one or more second peripheral edges to the pliable sheet material with one or more second seams.

In certain embodiments, the one or more first seams and the one or more second seams comprise one or more of adhesive seams, heat-welded seams, ultrasonically-welded seams, or sewn seams.

In certain embodiments, the surface covering member further comprises a first closing member joined to the first wrapper panel or joined to the pliable sheet material proximate to the first wrapper panel, and a second closing member joined to the second wrapper panel or joined to the pliable sheet material proximate to the second wrapper panel.

In certain embodiments, the first closing member is configured to maintain the first pouch and the compacted pliable sheet in a bundled state when the compacted pliable sheet is at least partially enveloped by the first pouch, and the second closing member is configured to maintain the second pouch and the compacted pliable sheet in a bundled state when the compacted pliable sheet is at least partially enveloped by the second pouch.

In certain embodiments, each of the first closing member and the second closing member comprises at least one of an adhesive surface or a portion of a hook-and-loop fastener.

In certain embodiments, wherein the pliable sheet material comprises one or more adhesive strips configured to permit the surface covering member to be adhered to a surface to be covered by the surface covering member.

In certain embodiments, the pliable sheet material is characterized by water impact resistance of no greater than 4.5 g when subjected to an American Association of Textile Chemists and Colorists 42 Impact Penetration test.

In certain embodiments, the first wrapper panel is affixed along the one or more first peripheral edges to the pliable sheet material with one or more first seams, and the second wrapper panel is affixed along the one or more second peripheral edges to the pliable sheet material with one or more second seams.

In certain embodiments, the one or more first seams and the one or more second seams comprise one or more of adhesive seams, heat-welded seams, ultrasonically-welded seams, or sewn seams.

In certain embodiments, a first closing member joined to the first wrapper panel or joined to the pliable sheet material proximate to the first wrapper panel, and a second closing member joined to the second wrapper panel or joined to the pliable sheet material proximate to the second wrapper panel.

In certain embodiments, the first closing member is configured to maintain the first pouch and the compacted pliable sheet in a bundled state when the compacted pliable sheet is at least partially enveloped by the first pouch, and the second closing member is configured to maintain the second pouch and the compacted pliable sheet in a bundled state when the compacted pliable sheet is at least partially enveloped by the second pouch.

In certain embodiments, each of the first closing member and the second closing member comprises at least one of an adhesive surface or a portion of a hook-and-loop fastener.

In certain embodiments, the pliable sheet material comprises one or more adhesive strips configured to permit the surface covering member to be adhered to a surface to be covered by the surface covering member.

In certain embodiments, the pliable sheet material is characterized by water impact resistance of no greater than 4.5 g when subjected to an American Association of Textile Chemists and Colorists 42 Impact Penetration test.

In certain embodiments, the surface covering member further comprises printed indicia on one or more of the first wrapper panel, the second wrapper panel, and the pliable sheet, the printed indica including instructions for use of the surface covering member to assist a user in at least partially enveloping the pliable sheet with one of the first pouch or the second pouch when the pliable sheet is compacted by rolling, folding, or stuffing.

In certain embodiments, at least a portion of one or more of the first wrapper panel and the second wrapper panel comprises at least one functional additive selected from the group consisting of antimicrobial agents and scented agents.

In certain embodiments, the surface covering member is embodied in a disposable healthcare drape, a disposable healthcare equipment cover, or a disposable equipment drape, or is embodied in one of the following disposable items: a flat or fitted bedding cover, a flat or fitted stretcher cover, a blanket, a seating surface cover, a tarpaulin, and absorbent pad, or an absorbent mat.

In another aspect, the disclosure relates to a surface covering member that includes a pliable sheet material, a wrapper panel, and at least one selectively deployable adhesive tab positioned on the wrapper panel. The pliable sheet material includes at least one liquid-penetration-resistant layer, and the wrapper panel comprises a continuous extension of the pliable sheet material along a first peripheral edge of the wrapper panel. The wrapper panel is configured to at least partially envelop the pliable sheet material when the pliable sheet material is compacted by one or more of rolling and folding, and the selectively deployable adhesive tab is configured to be deployed to maintain the compacted pliable sheet material in a state of being at least partially enveloped by the wrapper panel.

In certain embodiments, the selectively deployable adhesive tab is configured to affix a portion of the wrapper panel against a portion of the pliable sheet material when the surface covering member is in a non-compacted state.

In certain embodiments, wherein the wrapper panel is affixed to the pliable sheet material with one or more seams at second and third peripheral edges of the wrapper panel, wherein the one or more seams may comprise one or more of adhesive seams, heat-welded seams, ultrasonically-welded seams, or sewn seams.

In certain embodiments, the wrapper panel forms a pouch having a pouch opening.

In certain embodiments, the pliable sheet material is characterized by water impact resistance of no greater than 4.5 g when subjected to an American Association of Textile Chemists and Colorists 42 Impact Penetration test.

In certain embodiments, the pliable sheet material comprises one or more adhesive strips on the pliable sheet material and configured to permit the surface covering member to be adhered to a surface to be covered by the surface covering member.

In certain embodiments, the surface covering member further comprises printed indicia on at least one of the wrapper panel and the pliable sheet, the printed indica including instructions for use of the surface covering member to assist a user in at least partially enveloping the pliable sheet material with the wrapper panel when the pliable sheet material is compacted by one or more of rolling and folding.

In certain embodiments, at least a portion of the wrapper panel comprises at least one functional additive selected from the group consisting of antimicrobial agents and scented agents.

In certain embodiments, the surface covering member is embodied in a wearable protective garment configured to be worn by a human user; or is embodied in a disposable healthcare drape, a disposable healthcare equipment cover, or a disposable equipment drape; or is embodied in one of the following disposable items: a flat or fitted bedding cover, a flat or fitted stretcher cover, a blanket, a seating surface cover, a tarpaulin, and absorbent pad, or an absorbent mat.

In another aspect, the disclosure relates to a method for compacting a surface covering member comprising a pliable sheet material and a wrapper panel, the pliable sheet material including at least one liquid-penetration-resistant layer. The method includes multiple steps. One step includes removing the surface covering member from a covered surface. Another step includes folding and/or rolling opposing first and second edges of the surface covering member inward, and rolling the surface covering member with folded and/or rolled first and second edges in a direction from one of a third or fourth edge to an other of the third or fourth edge to place the surface covering member into a compacted state. Another step includes opening at least one selectively deployable adhesive tab joined to a wrapper panel to disengage at least a portion of the wrapper panel from the surface covering member. Another step includes at least partially enveloping the compacted surface covering member with the wrapper panel. Yet another step includes deploying the at least one selectively deployable adhesive tab to maintain the compacted pliable sheet material in a state of being at least partially enveloped by the wrapper panel.

In certain embodiments, the wrapper panel comprises a continuous extension of the pliable sheet material along a first peripheral edge of the wrapper panel.

In certain embodiments, the surface covering member is embodied in a wearable protective garment configured to be worn by a human user, and the removing of the surface covering member from the covered surface comprises removing the wearable protective garment from at least arms and a torso of the human user.

In certain embodiments, the surface covering member is embodied in a disposable healthcare drape, a disposable healthcare equipment cover, or a disposable equipment drape.

In certain embodiments, the surface covering member is embodied in one of the following disposable items: a flat or fitted bedding cover, a flat or fitted stretcher cover, a blanket, a seating surface cover, a tarpaulin, an absorbent pad, or an absorbent mat.

In another aspect, any features of the foregoing aspects and/or embodiments disclosed herein may be combined for additional advantage.

BRIEF DESCRIPTION OF DRAWINGS

FIG. 1A is a front elevational view of a surface covering member embodied in a protective garment including a wrapper panel having multiple edges with accordion folds and serving as a pouch along an interior of the protective garment, according to one embodiment of the present disclosure.

FIG. 1B is a magnified view of a portion of the wrapper panel and one accordion fold as shown in FIG. 1A.

FIG. 1C shows a wrapper panel according to FIG. 1A with addition of printed indicia.

FIG. 2A is a bottom plan view of a surface covering member including a wrapper panel along one edge thereof, according to one embodiment.

FIG. 2B is a bottom plan view of a surface covering member including first and second wrapper panels along or proximate to adjacent first and second edges of the surface covering member, according to one embodiment.

FIG. 2C is a bottom plan view of a surface covering member having first and second wrapper panels arranged proximate to, and inset from, opposing first and second edges of the surface covering member.

FIG. 2D is a bottom plan view of a surface covering member having first and second wrapper panels arranged at opposing first and second edges of the surface covering member.

FIGS. 12A-12D show a surface covering member in various states of being compacted (e.g., by folding and rolling) to be maintained in a compacted state with a non-pouch wrapper panel having a closing member at one end of the wrapper panel.

DETAILED DESCRIPTION

Figure 3A:
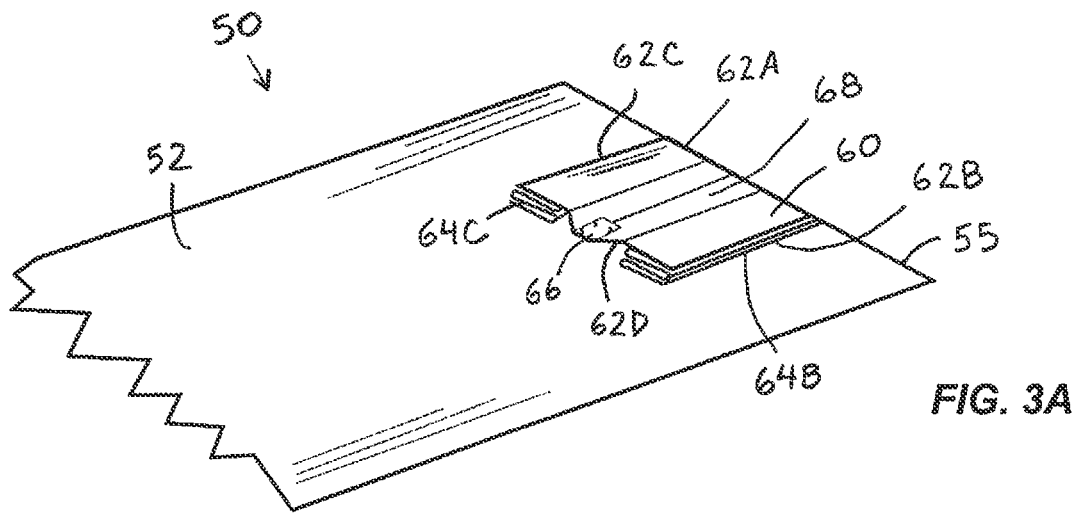
FIG. 3A is a bottom plan view of a portion of a surface covering member including a wrapper panel arranged at one end of a pliable sheet material, with the wrapper panel including accordion folds along multiple edges thereof to form a pouch, and with an adhesive closing member adhering one edge of the wrapper panel to the pliable sheet material.

Aspects of the present disclosure are directed to a surface covering member that includes a pliable sheet material and a wrapper panel, with the pliable sheet material including at least one liquid-penetration-resistant layer, wherein the wrapper panel (which may or may not comprise a pouch) may be used to at least partially envelop the pliable sheet material when the pliable sheet material is compacted. Various types of surface covering members are included within the scope of the disclosure, including, but not limited to, wearable protective garments configured to be worn by human users, disposable healthcare drapes, a disposable healthcare equipment covers, disposable equipment drapes, and various disposable items such as flat or fitted bedding covers, flat or fitted stretcher covers, blankets, seating surface covers, tarpaulins, absorbent mats, and the like.

In certain embodiments, a pliable sheet material comprises one or more polymeric material layers such as a meltbonded, spunbonded, or SMS (spin-melt-spin) polymer layer. Examples of suitable materials include polyolefins generally, such as polypropylene, polyethylene, and combinations thereof. The one or more polymeric material layers may embody one or more one liquid-penetration-resistant layer to cause the pliable sheet material to resist penetration of liquids. The Association for the Advancement of Medical Instrumentation (AAMI) has promulgated standards designed to help medical device companies meet global standards for safe use of medical devices, including the voluntary standard ANSI/AAMI PB70:2012, entitled "Liquid Barrier Performance and Classification of Protective Apparel and Drapes Intended for Use in Health Care Facilities," to determine identification measures for the selection of protective apparel and drapes (including but not limited to medical gowns, for use in healthcare facilities. AAMI classifications step from four levels of barrier performance, measured according to the following standardized tests:

(1) AATCC 42-2017: Measures resistance of fabrics to the penetration of water by impact (AATCC, 2018);
(2) AATCC 127-2017: Measures resistance of fabric to the penetration of water under hydrostatic pressure (AATCC, 2017);

(3) ASTM F1670-17: Evaluate resistance of materials used in protective clothing to penetration by synthetic blood under conditions of continuous liquid contact (ASTM, 2017); and (4) ASTM F1671-13: Measure penetration by bloodborne pathogens using a surrogate microbe under conditions of continuous liquid contact (ASTM, 2013).

Surface covering members as described herein may meet one or more of the barrier performance Levels 1 to 4 as defined in the following Table 1. In certain embodiments, surface covering members may, at a minimum, be characterized by water impact resistance of no greater than 4.5 g when subjected to an American Association of Textile Chemists and Colorists 42 Impact Penetration test (AATCC 42). Optionally, surface covering members may be characterized by spray impact resistance of no greater than 1.0 g when subjected to AATCC 42, optionally combined being characterized by hydrostatic pressure resistance of greater than 20 cm, or greater than 50 cm, when subjected to AATCC 127. Optionally, surface covering members may pass tests according to ASTM F1670 and/or ASTM F1671.

TABLE 1

| Barrier Performance | Barrier Protection | Resistance Measures | Test | Test Criteria | Acceptable Quality Level |
| --- | --- | --- | --- | --- | --- |
| Level 1 | Minimal | Liquid Penetration | AATCC 42 | Water Impact ≤4.5 g | 4% |
| Level 2 | Low | Liquid Penetration | AATCC 42 | Spray Impact ≤1.0 g | 4% |
|  |  |  | AATCC 127 | Hydrostatic Pressure ≥20 cm | 4% |
| Level 3 | Moderate | Liquid Penetration | AATCC 42 | Spray Impact ≤1.0 g | 4% |
|  |  |  | AATCC 127 | Hydrostatic Pressure ≥50 cm | 4% |
| Level 4 | High | Liquid and Viral Penetration | ASTM F1671 | Pass | 4% |

A pliable sheet material may include one or more additional layers and/or one or more functional additives. In certain embodiments, one or more additional layers may include an absorbent material layer.

Surface covering members according to embodiments herein include, in addition to a pliable sheet material, at least one wrapper panel, wherein each wrapper panel is engaged along one or more peripheral edges thereof to the pliable sheet material. A wrapper panel is configured to at least partially envelop the pliable sheet material when the pliable sheet material is compacted (e.g., by one more of rolling and folding, or one or more of rolling, folding, and stuffing, in various embodiments). In certain embodiments, a wrapper panel is engaged along multiple peripheral edges to a pliable sheet material, with at least one peripheral edge not being permanently engaged to the wrapper panel. In certain embodiments, a wrapper panel forms a pouch with one peripheral edge not engaged permanently to the pliable sheet material. In certain embodiments, a wrapper panel is engaged along a single peripheral edge to a pliable sheet material without forming a pouch.

In certain embodiments, in use, a wrapper panel is configured to be placed along an inner face (or underside) of a pliable sheet material arranged to contact a surface to be covered. Restated, a wrapper panel is configured to be arranged between a surface to be covered and a pliable sheet material. In this manner, after an outer face of a pliable sheet material is soiled, the surface covering member may be compacted (e.g., by one or more of rolling and folding (for non-pouch wrapper panel embodiments), or one or more of rolling, folding, and stuffing (for pouch-type wrapper panel embodiments), and then at least partially enveloped by the wrapper panel, with the wrapper panel not being previously exposed to contaminants such as biological fluids.

In certain embodiments, a wrapper panel may be permanently affixed to a pliable sheet material with one or seams along one or more (but less than all) peripheral edges of the wrapper panel, which may comprise one or more of adhesive seams, heat-welded seams, ultrasonically-welded seams, or sewn seams, wherein single or double seams may be provided along individual peripheral edges. In certain embodiments, a wrapper panel having four peripheral edges may be permanently engaged to a pliable sheet material along first, second, and third edges of the wrapper panel, but not along a fourth edge of the wrapper panel. In certain embodiments, a wrapper panel may be configured to form a pouch with a pouch opening. In certain embodiments, one or more unbound peripheral edges of a wrapper panel may be temporarily or removably affixed to a pliable sheet material with an adhesive surface and/or a portion of a hook-and-loop fastener, optionally wherein the adhesive surface and/or hood-and-loop fastener may embody (or be part of) a closing member configured to maintain the pliable sheet material in a compacted state. In certain embodiments, a wrapper panel comprising multiple peripheral edges may be permanently engaged to a pliable sheet material along a first edge, and temporarily or removable affixed to the pliable sheet material along one or more of the other peripheral edges.

In certain embodiments, a wrapper panel comprises a continuous extension of the pliable sheet material, along a first peripheral edge of the wrapper panel. For example, portion of a pliable sheet material intended to form a wrapper panel may be folded over a remainder of the pliable sheet material (whether including a simple fold or an accordion fold) to form one peripheral edge of the wrapper panel. In certain embodiments, one or more other peripheral edges of such a wrapper panel (e.g., including a continuous extension of a pliable sheet material) may be permanently affixed to the pliable sheet material with one or more seams, which may comprise one or more of adhesive seams, heat-welded seams, ultrasonically-welded seams, or sewn seams, wherein single or double seams may be provided along individual peripheral edges. In certain embodiments, one or more peripheral edges of a wrapper panel (e.g., including a continuous extension of a pliable sheet material) may be temporarily or removably affixed to a pliable sheet material with an adhesive surface and/or a portion of a hook-and-loop fastener, optionally wherein the adhesive surface and/or hood-and-loop fastener may embody (or be part of) a closing member configured to maintain the pliable sheet material in a compacted state.

In certain embodiments, a wrapper panel is permanently engaged to a pliable sheet material with one or more accordion folds along one or more peripheral edges of the wrapper panel. Presence of such accordion fold(s) may beneficially provide increased volume for the wrapper panel (whether or not configured as a pouch) to receive and at least partially envelop a compacted pliable sheet material, thereby enhancing ease of use. In certain embodiments, a single accordion fold is provided; first and second accordion folds are provided; or first to third accordion folds are provided, along portions of a perimeter of a wrapper panel. In certain embodiments, a wrapper panel may comprise a variable width, wherein increased width regions of a wrapper panel may be utilized to form accordion folds when the wrapper panel is affixed to a pliable sheet material.

In certain embodiments, at least one closing member is joined to one or more of the wrapper panel and the pliable sheet material, with the closing member(s) being configured to maintain the wrapper panel and the pliable sheet material in a bundled state with the compacted pliable sheet being at least partially enveloped by the wrapper panel. In certain embodiments, a closing member comprises at least one of an adhesive surface or a portion of a hook-and-loop fastener. In certain embodiments, a closing member comprises one or more elongated ties joined to one or more of the wrapper panel and the pliable sheet material. In certain embodiments, a perforated region of a surface covering member (e.g., a perforated region of a pliable sheet material) proximate to a wrapper panel may be configured to form at least one elongated closing member upon partial detachment from a remainder of the surface covering member. In certain embodiments, one or more elongated ties may be combined with adhesive surfaces and/or portions of hood-and-loop fasteners to form closing members. For example, elongated ties may include adhesive regions and/or hook-and-loop fastener regions to serve as closing members.

In certain embodiments, at least one peripheral edge of a wrapper panel may include a non-permanent adhesive region, optionally embodied in selectively deployable adhesive tabs. Such non-permanent adhesive regions (e.g., selectively deployable adhesive tabs) may be configured to affix one or more peripheral edges against portions of the pliable sheet material when the surface covering member is in a non-compacted state, and may also be deployed to maintain the compacted pliable sheet material in a state of being at least partially enveloped by the wrapper panel, following compaction of the pliable sheet material.

If multiple wrapper panels are provided, then in certain embodiments, a surface covering member may include multiple closing members, including at least one first closing member joined to a first wrapper panel or joined to the pliable sheet material proximate to the first wrapper panel, and including at least one second closing member joined to a second wrapper panel or joined to the pliable sheet material proximate to the second wrapper panel. In such an embodiment, the first closing member may be configured to maintain the first pouch and the compacted pliable sheet in a bundled state when the compacted pliable sheet is at least partially enveloped by the first wrapper panel (optionally forming a first pouch), while the second closing member may be configured to maintain the second pouch and the compacted pliable sheet in a bundled state when the compacted pliable sheet is at least partially enveloped by the second wrapper panel (optionally forming a second pouch).

In certain embodiments, a surface covering member may include multiple wrapper panels, such as a first wrapper panel located at a first position on a pliable sheet member and a second wrapper panel located at a second position on the pliable sheet member, wherein each wrapper panel may be individually arranged to at least partially envelop the pliable sheet material when it is in a compacted state. This may be beneficial to permit a pliable sheet material to be compacted (e.g., folded, rolled, and/or stuffed) from different directions, depending on circumstances such as physical accessibility and/or where biological contamination may be present on a pliable sheet material. For example, a surface covering material embodied in a stretcher sheet, an equipment drape, or a floor covering may be fitted over an underlying surface in any suitable direction, wherein presence of multiple wrapper panels may permit a user to initiate compaction of a soiled surface covering material in multiple possible directions, thereby reducing the burden to the user of determining location of a wrapper panel before initiating removal and compaction of the surface covering member, and/or reducing the possibility that user would need to un-compact and re-compact a soiled surface covering member in preparation for disposal. In certain embodiments, first and second wrapper panels may be arranged along or proximate to first and second opposing edges of a pliable sheet material. In certain embodiments, first and second wrapper panels may be arranged along or proximate to first and second adjacent edges of a pliable sheet material.

In certain embodiments, a surface covering member may include printed indicia (e.g., text, pictures, diagrams, arrows, etc.) on at least one of the wrapper panel and pliable sheet, with the printed indicia including instructions for use of the surface covering member (and/or including identification of location(s) of one or more wrapper panels) to assist a user in at least partially enveloping the pliable sheet material with the wrapper panel when the pliable sheet material is compacted by rolling, folding, or stuffing. Such printed indicia may reduce the burden to the user in determining location of a wrapper panel before initiating removal and compaction of the surface covering member, and/or reduce the possibility that user would need to un-compact and re-compact a soiled surface covering member in preparation for disposal.

In certain embodiments, at least a portion of a wrapper panel, and/or at least a portion of a surface covering member, may include at least one functional additive such as an antimicrobial agent and a scented agent, wherein such additive(s) may be impregnated, coated, or otherwise added by any suitable means. Presence of antimicrobial agents may reduce numbers of live bacteria, viruses, or the like on a soiled surface covering member (e.g., when in a compacted state, for a functional additive present solely on a wrapper panel). Scented agents may reduce perceptible odor associated with a soiled surface covering member (e.g., when in a compacted state, for a functional additive present solely on a wrapper panel).

In certain embodiments, a pliable sheet material may include one or more adhesive regions (e.g., adhesive strips) to permit a surface covering member to be adhered to an underlying surface (of an article such as floor, equipment, seat, etc.) to be covered by the surface covering member. Such adhesive regions may be used to maintain position and/or prevent slipping of a surface covering member, which may be particularly useful for floor and seating surface covering members.

In certain embodiments, at least a portion of a pliable sheet material may include an absorbent material in addition to a liquid-penetration-resistant layer, to serve as an absorbent mat or an absorbent pad.

Various features of surface covering members are shown in the accompanying figures.

FIG. 1A is a front elevational view of a surface covering member 10 embodied in a protective garment, including a pliable sheet material 12 and a wrapper panel 20 affixed to the pliable sheet material 12 to serve as a pouch. The pliable sheet material 12 includes an inner surface 13 and an outer surface 14, wherein the wrapper panel 20 is affixed to the inner surface 13 proximate to a lower edge 15 of the pliable sheet material 12. The protective garment includes a head/neck opening 17, arm portions 18, and a torso portion 19 formed of the pliable sheet material 12. The wrapper panel 20 includes peripheral edges 22A to 22D, with opposing side peripheral edges 22B, 22C each having associated accordion folds 24B, 24C between the wrapper panel 20 and the pliable sheet material 12. A first peripheral edge 22A is permanently affixed to the pliable sheet material 12, whereas a fourth peripheral edge 22D is not, but optionally the fourth peripheral edge 22D may be removably affixed to the pliable sheet material 12 with a closing member 26 that may include an adhesive surface or a portion of a hook-and-loop fastener. The wrapper panel 20 (including open or openable peripheral edge 22D) may therefore form a pouch that may be expanded in volume with the accordion folds 24B, 24B along second and fourth peripheral edges 22B, 22C of the wrapper panel 20.

FIG. 1B is a magnified view of a portion of the wrapper panel 20 and one accordion fold 24B of the surface covering member 10 shown in FIG. 1A. The wrapper panel 20 may include an outer panel surface 21 and an inner panel surface 23, wherein the inner panel surface 23 may be positioned adjacent to the inner surface (13 in FIG. 1A) of a pliable sheet material (12 in FIG. 1A). A seam 25B may be provided permit joining between the accordion fold 24B and a portion of the pliable sheet material (12 in FIG. 1A).

FIG. 1C shows a wrapper panel 20 according to FIG. 1A with addition of printed indicia 29, which may be either arranged directly on the wrapper panel 20 or on a label 28. In certain embodiments, the printed indicia may include instructions for use of the surface covering member, including but not limited to text, pictures, diagrams, arrows, and the like, to assist a user in at least partially enveloping a pliable sheet material (12 in FIG. 1A) with the wrapper panel 20 when the pliable sheet material (12 in FIG. 1A) is compacted by rolling, folding, or stuffing. In certain embodiments, printed indicia may alternatively or additionally be provided on portions of a pliable sheet material, and may include use instructions and/or identification of location(s) of one or more wrapper panels.

FIG. 2A is a bottom plan view of a surface covering member 30A including a wrapper panel 40 along one edge 35A (of four edges 35A-35D) of a pliable sheet material 32 The wrapper panel 40 includes four peripheral edges 42A-42D and a closing member 46, with a first peripheral edge 42A of the wrapper panel 40 coinciding with a first edge 35A (and optionally being a continuous extension) of the pliable sheet material 32. At least one peripheral edge (e.g., peripheral edges 42A-1, 42A-2), but less than all of the peripheral edges 42A-42D of the wrapper panel 40, is/are permanently affixed to the pliable sheet material 32. Optionally, the wrapper panel 40 may form a pouch with an open (or openable) peripheral edge 42D.

FIG. 2B is a bottom plan view of a surface covering member 30B including a first wrapper panel 40-1 arranged proximate to (but inset from) a first edge 35A of a pliable sheet material 32, and including a second wrapper panel 40-2 along a second edge 35B of the pliable sheet material 32. The first wrapper panel 40-1 includes four peripheral edges 42A-1 to 42D-1 and a closing member 46-1, with a first peripheral edge 42A-1 being parallel to the first edge 35A of the pliable sheet material 32. The second wrapper panel 40-2 includes four peripheral edges 42A-2 to 42D-2 and a closing member 46-2, with a first peripheral edge 42A-2 being coincident with a second edge 35B of the pliable sheet material 32 (and optionally being a continuous extension of the pliable sheet material 32). As shown, the wrapper panels 40-1, 40-2 are arranged along or proximate to two adjacent edges 35A, 35B of the pliable sheet material 32. For each wrapper panel 40-1, 40-2, at least one peripheral edge (e.g., peripheral edges 42A-1, 42A-2), but less than all of the peripheral edges 42A-1 to 42D-1, 42A-2 to 42D-2, is/are permanently affixed to the pliable sheet material 32. Optionally, each wrapper panel 40-1, 40-2 may form a pouch with an open (or openable) peripheral edge 42D-1, 42D-2.

FIG. 2C is a bottom plan view of a surface covering member 30C including first and second wrapper panels 40-1, 40-2 arranged proximate to (but inset from) opposing edges 35A, 35D, respectively, of a pliable sheet material 32 that includes four edges 35A-35D. Each wrapper panel 40-1, 40-2 includes four peripheral edges 42A-1 to 42D-1, 42A-2 to 42D-2 and a closing member 46-1, 46-2. For each wrapper panel 40-1, 40-2, at least one, but less than all, of the peripheral edges 42A-1 to 42D-1, 42-A-2 to 42D-2 is/are permanently affixed to the pliable sheet material 32. Each wrapper panel 40-1, 40-2 includes four peripheral edges 42A-1 to 42D-1, 42A-2 to 42D-2 and a closing member 46-1, 46-2, with each wrapper panel 40-1, 40-2 including one peripheral edge 42A-1, 42A-2 near an edge 35A, 35D of the pliable sheet material 32. For each wrapper panel 40-1, 40-2, at least one peripheral edge (e.g., peripheral edges 42A-1, 42A-2), but less than all of the peripheral edges 42A-1 to 42D-1, 42A-2 to 42D-2, is/are permanently affixed to the pliable sheet material 32. Optionally, each wrapper panel 40-1, 40-2 may form a pouch with an open (or openable) peripheral edge 42D-1, 42D-2

FIG. 2D is a bottom plan view of a surface covering member 30D having first and second wrapper panels 40-1, 40-2 arranged at opposing 35A, 35D, respectively, of a pliable sheet material 32 that includes four edges 35A-35D. Each wrapper panel 40-1, 40-2 includes four peripheral edges 42A-1 to 42D-1, 42A-2 to 42D-2 and a closing member 46-1, 46-2, with each wrapper panel 40-1, 40-2 including one peripheral edge 42A-1, 42A-2 coincident with an edge 35A, 35D of the pliable sheet material 32 (and optionally embodying a continuous extension of the pliable sheet material 32). For each wrapper panel 40-1, 40-2, at least one peripheral edge (e.g., peripheral edges 42A-1, 42A-2), but less than all of the peripheral edges 42A-1 to 42D-1, 42A-2 to 42D-2, is/are permanently affixed to the pliable sheet material 32. Optionally, each wrapper panel 40-1, 40-2 may form a pouch with an open (or openable) peripheral edge 42D-1, 42D-2.

Figure 3B:
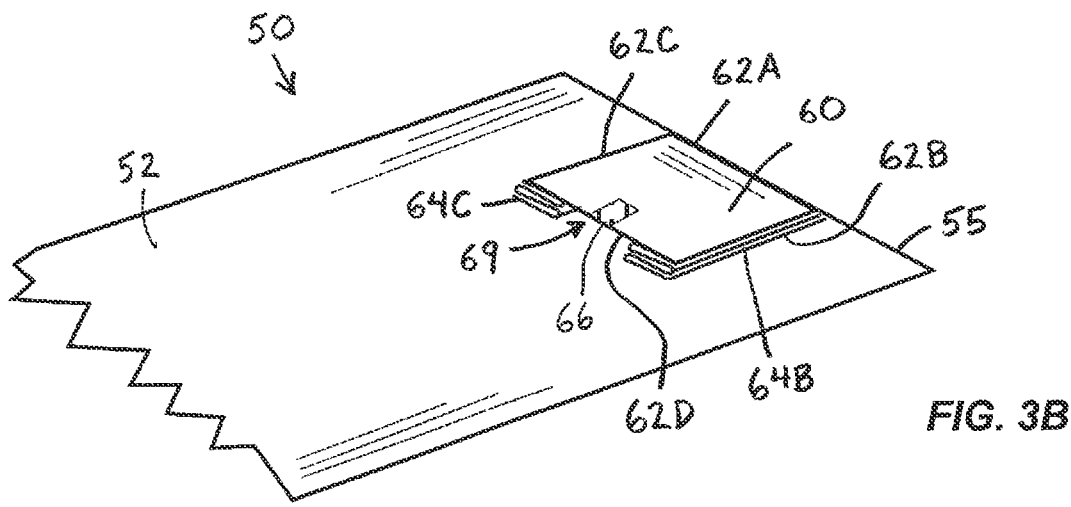
FIG. 3B is a bottom plan view of the surface covering member portion of FIG. 3A with the adhesive closing member separated from the pliable sheet material.

FIG. 3A is a bottom plan view of a portion of a surface covering member 50 including a wrapper panel 60 arranged along one end 55 of a pliable sheet material 52, with the wrapper panel 60 affixed to the pliable sheet material 52 at first to third peripheral edges 62A-62C to form a pouch, with accordion folds 64B, 64C along multiple peripheral edges 62B, 62C of the wrapper panel. As illustrated, a selectively deployable adhesive closing member 66 is provide at a fourth peripheral edge 62D of the wrapper panel 60 to temporarily adhere the wrapper panel 60 to the pliable sheet material 52, causing a central portion 68 of the wrapper panel 60 to contact the pliable sheet material 52. FIG. 3B shows the items of FIG. 3A, the selectively deployable adhesive closing member 66 being separated from the pliable sheet material 52 to form an opening 69 into a pouch formed by the wrapper panel 60.

Figure 4:
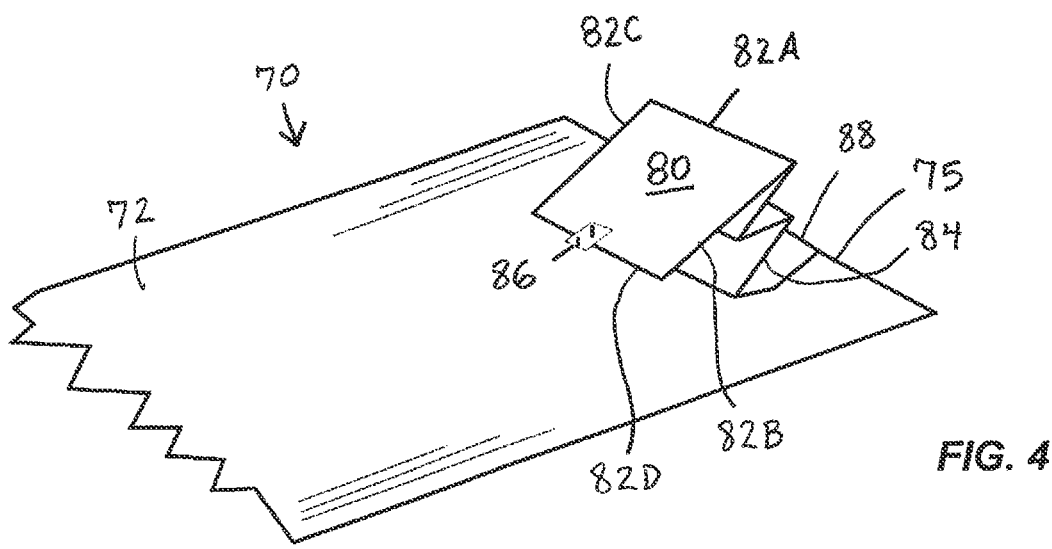
FIG. 4 is a bottom plan view of a portion of a surface covering member including a wrapper panel arranged at one end thereof (without the wrapper panel forming a pouch), with the wrapper panel including a single accordion fold and including an adhesive closing member adhering one edge of the wrapper panel to the surface covering member.

FIG. 4 is a bottom plan view of a portion of a surface covering member 70 including a wrapper panel 80 arranged at one end 75 of a pliable sheet material 72. The wrapper panel 80 includes first to fourth peripheral edges 82A-82D, with an accordion fold 84 arranged between a first peripheral edge 82A and the end 75 of the pliable sheet material 72. Optionally, the wrapper panel 80 (and/or the accordion fold 84) may embody a continuous extension of the pliable sheet material 72, or at least one seam 88 may be provided between the accordion fold 84 and the pliable sheet material 72. A selectively deployable adhesive closing member 86 may be provided to adhere the wrapper panel 80 to the pliable sheet material when the surface covering member 70 is in an uncompacted state, wherein the selectively deployable adhesive closing member 86 may also be used to maintain the surface covering member 70 in a bundle stated when the surface covering member 70 is compacted (e.g., by rolling and/or folding) and at least partially enveloped by the wrapper panel 80 (with such enveloping optionally including the accordion fold 84).

In certain embodiments, one or more perforated regions may be formed in a surface covering member (e.g., in a pliable sheet material and/or a wrapper panel) to form outlines of one or more elongated closing members that may be partially detached from the surface covering member and used to maintain the surface covering member in a bundle stated when the surface covering member is compacted after use. Examples of such an arrangement are shown in FIGS. 5A-5B and FIG. 6.

Figure 5A:
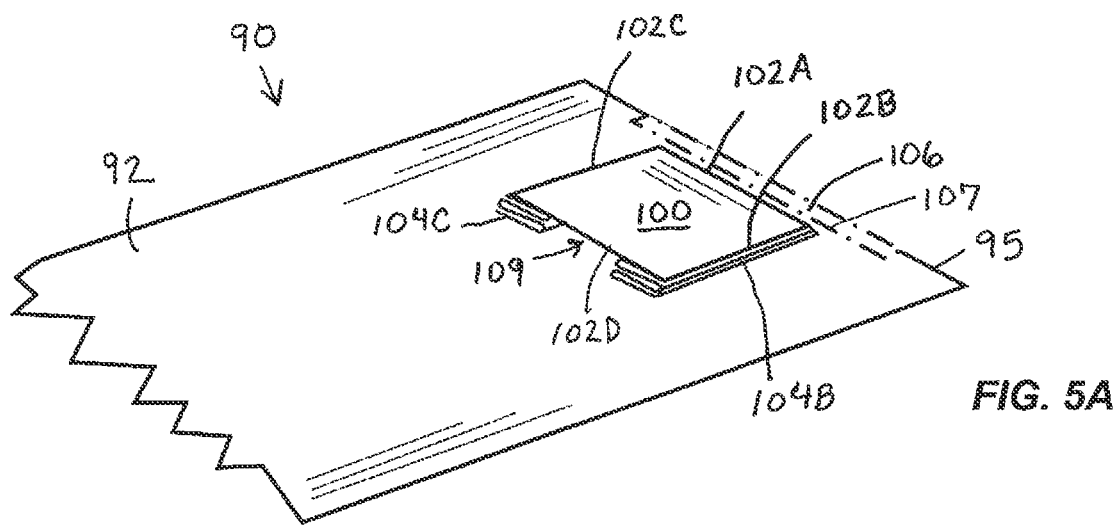
FIG. 5A is a bottom plan view of a portion of a surface covering member including a wrapper panel inset from a first edge thereof, with a perforated region of the surface covering member being configured to form at least one elongated closing member when partially detached from a remainder of the surface covering member.
Figure 5B:
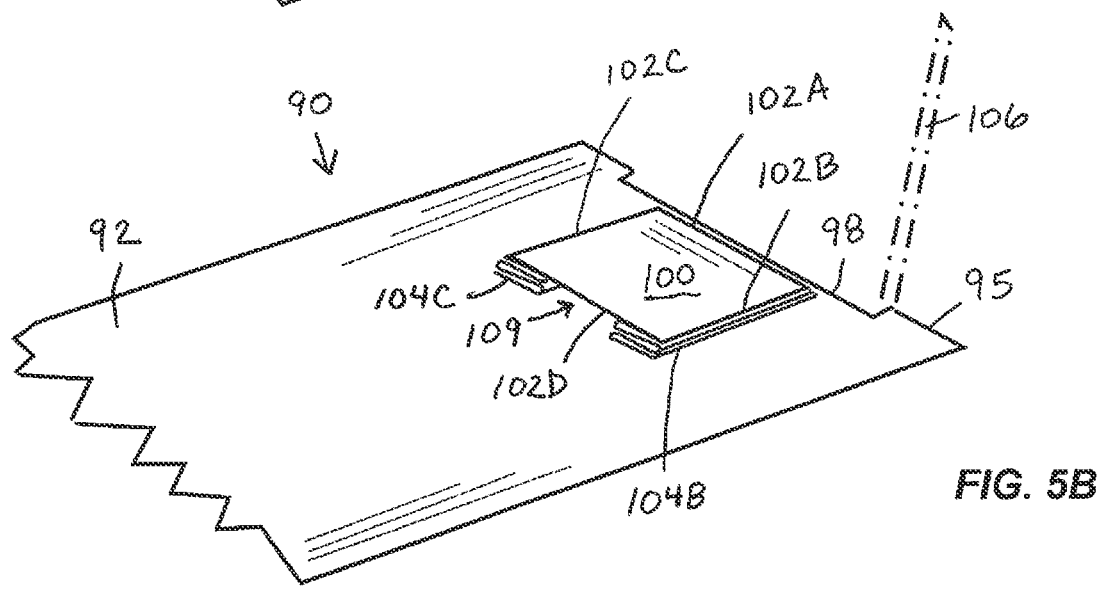
FIG. 5B illustrates the surface covering member of FIG. 5A following partial detachment of a perforated region of the surface closing member to form one elongated closing member.

FIG. 5A is a bottom plan view of a portion of a surface covering member 90 including a wrapper panel 100 inset from a first edge 95 of a pliable sheet material 92, with a perforated region 107 of the pliable sheet material 92 being configured to form at least one elongated closing member 106 when partially detached from a remainder of the surface covering member 90. As shown, the wrapper panel 100 is affixed to the pliable sheet material 92 at first to third peripheral edges 102A-102C to form a pouch having a pouch opening 109, with accordion folds 104B, 104C along multiple peripheral edges 102B, 102C of the wrapper panel 100. FIG. 5B illustrates the surface covering member 90 of FIG. 5A following partial detachment of the perforated region (107 in FIG. 5A) of the pliable sheet material 92 to form an elongated closing member 106. Optionally, the elongated closing member 106 may include adhesive and/or portions of a hook-and-loop fastener to effectuate closing of a bundle after the pliable sheet material is compacted into a pouch formed by the wrapper panel 100, or the elongated closing member 106 may be used as a tie to form a knot or the like around the bundle-containing pouch.

Figure 6:
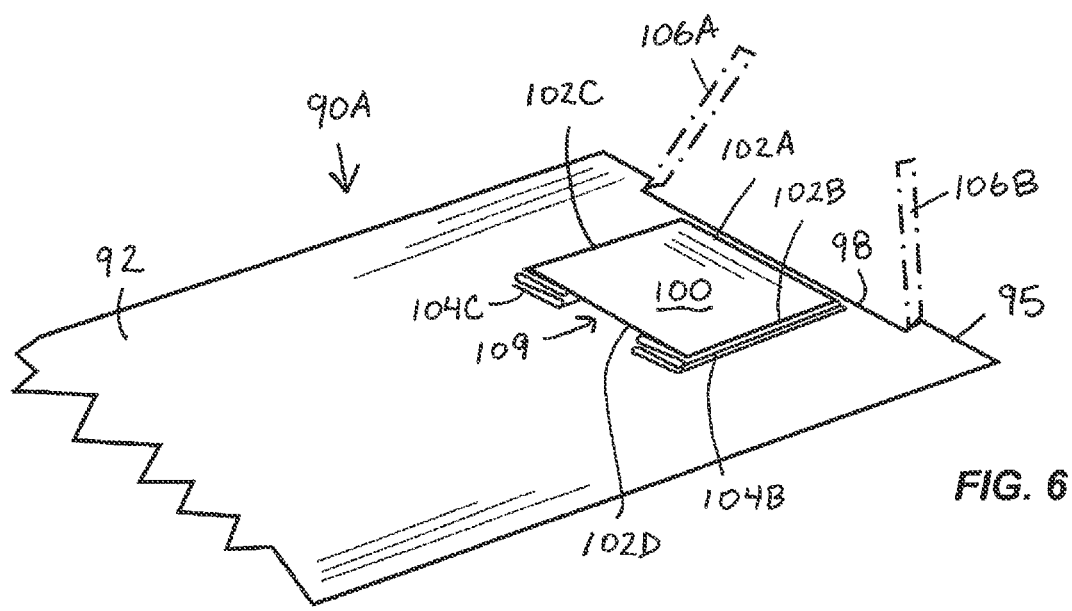
FIG. 6 illustrates a surface covering member similar to the one shown in FIG. 5A, following partial detachment of first and second perforated regions of the closing member to form first and second elongated closing members.

In certain embodiments, portions of a surface covering member may be partially detached to form multiple elongated closing members, such as shown in FIG. 6. FIG. 6 illustrates a surface covering member 90A similar to the surface covering member 90 shown in FIG. 5A, following partial detachment of first and second perforated regions of the pliable sheet material 92 to form first and second elongated closing members 106A, 106B.

Figure 7A:
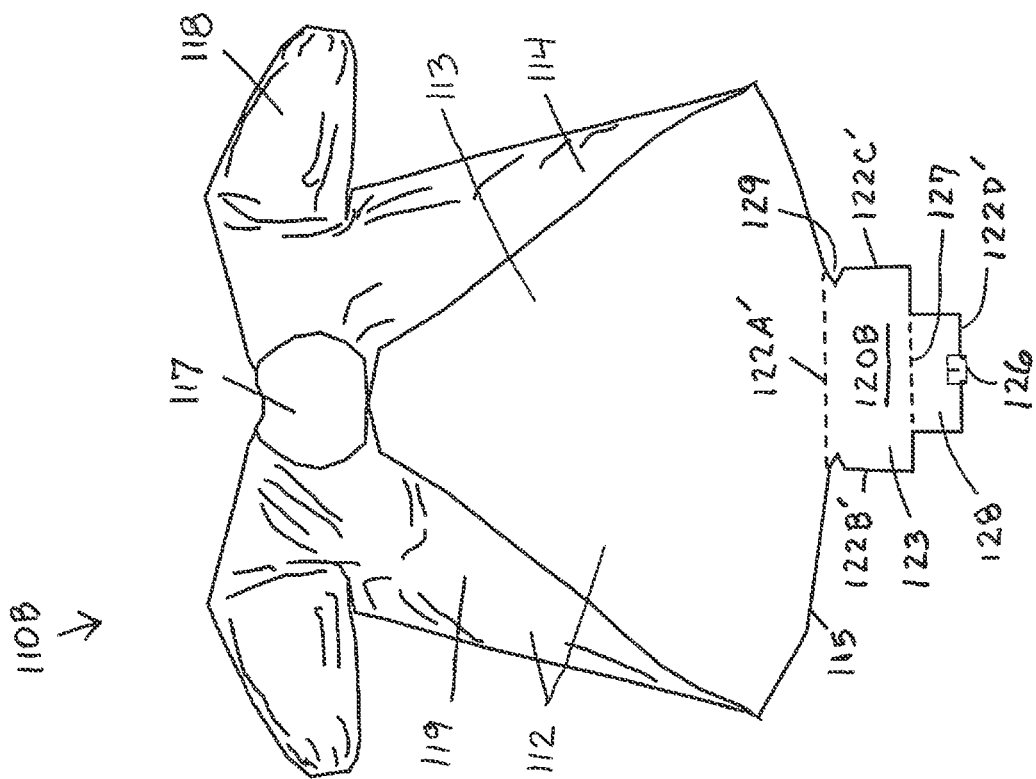
FIG. 7A is a front elevational view of a surface covering member embodied in a protective garment including a constant width wrapper panel as a continuous extension of the pliable sheet material, with a closing member arranged at one end of the wrapper panel, according to one embodiment.

FIG. 7A is a front elevational view of a surface covering member 110A embodied in a protective garment, including a pliable sheet material 112 and a constant width wrapper panel 120A as a continuous extension of the pliable sheet material 112. The pliable sheet material 112 includes an inner surface 113 and an outer surface 114, wherein the wrapper panel 120A extends continuously from a lower edge 115 of the pliable sheet material 112. The protective garment includes a head/neck opening 117, arm portions 118, and a torso portion 119 formed of the pliable sheet material 112. The wrapper panel 120A includes peripheral edges 122A to 122D, wherein a first peripheral edge 122A is configured to form a fold (e.g., a single fold) with the pliable sheet material 112. An inner surface 123 of the wrapper panel is shown. The fourth peripheral edge 122D of the wrapper panel 120A may be removably affixed to (the inner surface 113 of) the pliable sheet material 112 with a closing member 126 that may include an adhesive surface or a portion of a hook-and-loop fastener. Optionally, when the wrapper panel 120A is folded upward along the first peripheral edge 122A, the second and third peripheral edges 122B, 122C of the wrapper panel 120A may be removably or permanently affixed to the inner surface 123 of the pliable sheet material 112 to form a pouch. Alternatively, the second and third peripheral edges 122B, 122C may remain unattached relative to the pliable sheet material 112.

Figure 7B:
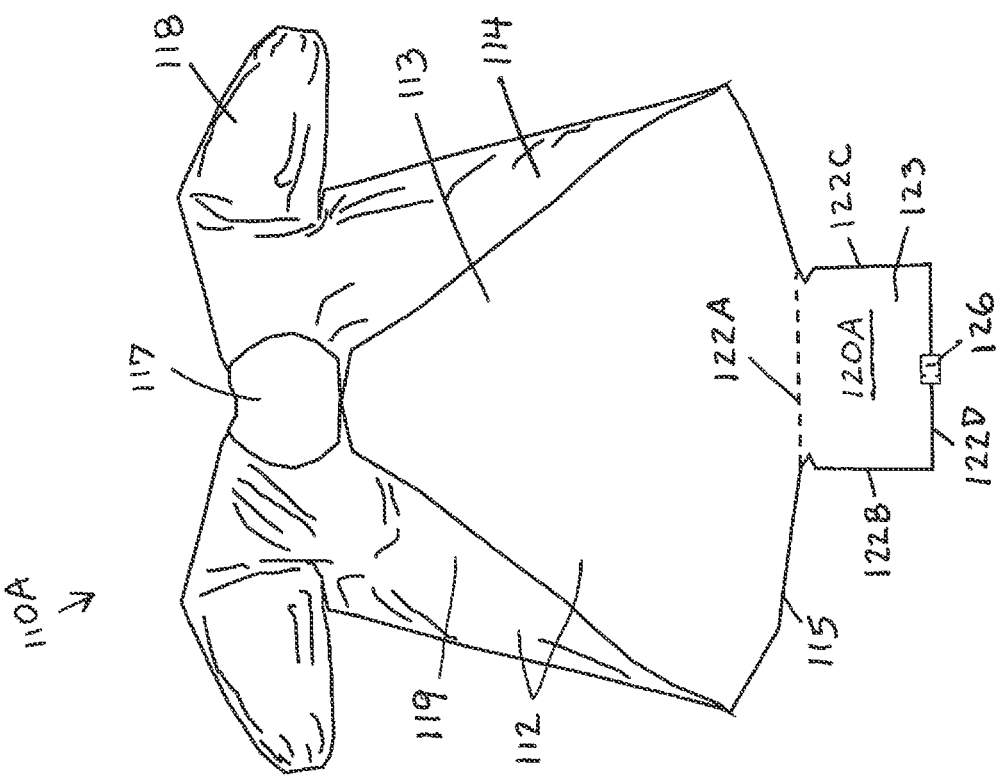
FIG. 7B is a front elevational view of a surface covering member embodied in a protective garment being similar to that shown in FIG. 7A, but with the wrapper panel including a variable width, including a reduced width distal portion that may be tucked into a pouch when the wrapper panel is affixed to the pliable sheet material.

FIG. 7B is a front elevational view of a surface covering member 110B embodied in a protective garment being similar to that shown in FIG. 7A, but with the wrapper panel 120B including a variable width, including a reduced width distal portion 128 that may be tucked (along intermediate fold line 127) into a pouch if (and when) the wrapper panel 120B is affixed along second and third edges 122B', 122C' to the pliable sheet material 112. If desired, an accordion fold (not shown) may be provided at the intermediate fold line 127. The wrapper panel 120B is a continuous extension of the pliable sheet material 112. The pliable sheet material 112 includes an inner surface 113 and an outer surface 114, wherein the wrapper panel 120B extends continuously from a lower edge 115 of the pliable sheet material 112. The protective garment includes a head/neck opening 117, arm portions 118, and a torso portion 119 formed of the pliable sheet material 112. The wrapper panel 120B includes peripheral edges 122A' to 122D', wherein a first peripheral edge 122A is configured to form a fold (e.g., a single fold) with the pliable sheet material 112. Inset transition portions 129 are provided between a first peripheral edge 122A' and second and third peripheral edges 122B', 122C', wherein the inset portions 129 may aid in forming accordion folds along the second and third peripheral edges 122B', 122C', if desired. An inner surface 123 of the wrapper panel is shown. The fourth peripheral edge 122D' of the wrapper panel 120B may be removably affixed to (the inner surface 113 of) the pliable sheet material 112 with a closing member 126 that may include an adhesive surface or a portion of a hook-and-loop fastener. Optionally, when the wrapper panel 120B is folded upward along the first peripheral edge 122A', the second and third peripheral edges 122B', 122C' of the wrapper panel 120A may be removably or permanently affixed to the inner surface 123 of the pliable sheet material 112 to form a pouch into which the distal portion 128 may be tucked.

Figure 8A:
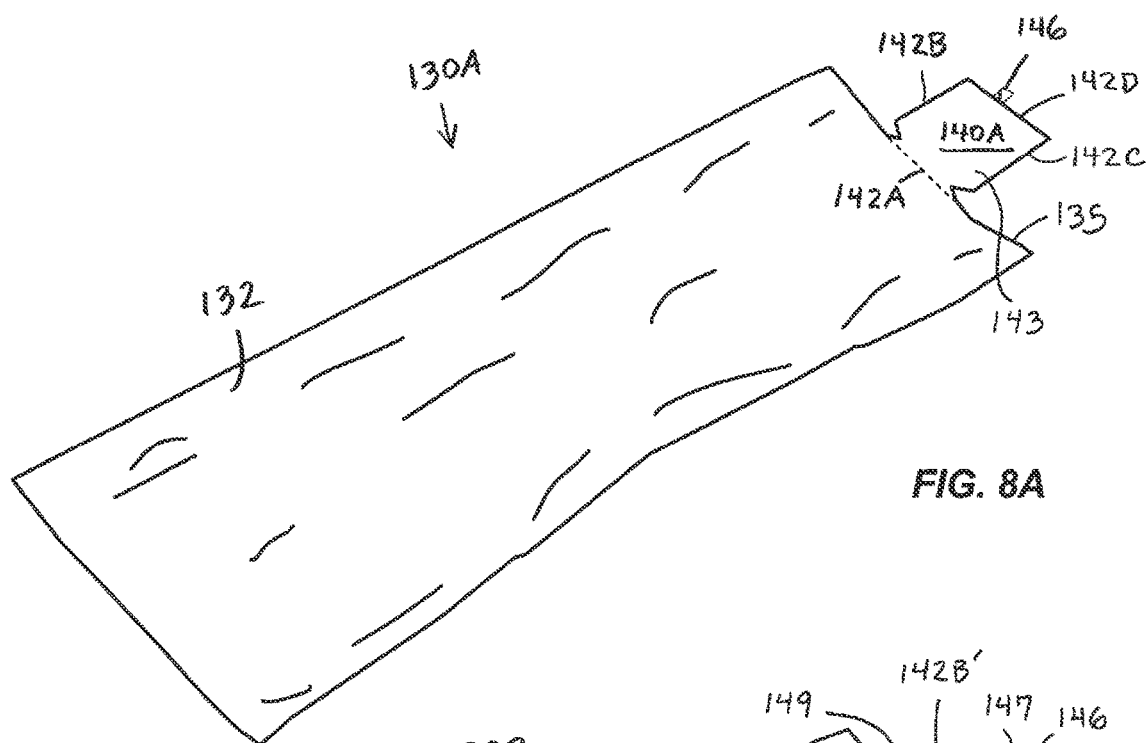
FIG. 8A is a bottom plan view of a generally rectangular surface covering member including a constant width wrapper panel as a continuous extension of the pliable sheet material, with a closing member arranged at one end of the wrapper panel, according to one embodiment.

FIG. 8A is a bottom plan view of a generally rectangular surface covering member 130A including a constant width wrapper panel 140A as a continuous extension of a pliable sheet material 132 at an end 135 thereof. The wrapper panel 140A includes peripheral edges 142A to 142D, wherein a first peripheral edge 142A is configured to form a fold (e.g., a single fold) with the pliable sheet material 132. An inner surface 143 of the wrapper panel is shown. The fourth peripheral edge 142D of the wrapper panel 140A may be removably affixed to (the inner surface 143 of) the pliable sheet material 132 with a closing member 146 that may include an adhesive surface or a portion of a hook-and-loop fastener. Optionally, when the wrapper panel 140A is folded upward along the first peripheral edge 142A, the second and third peripheral edges 142B, 142C of the wrapper panel 140A may be removably or permanently affixed to the inner surface 143 of the pliable sheet material 132 to form a pouch. Alternatively, the second and third peripheral edges 142B, 142C may remain unattached relative to the pliable sheet material 132.

Figure 8B:
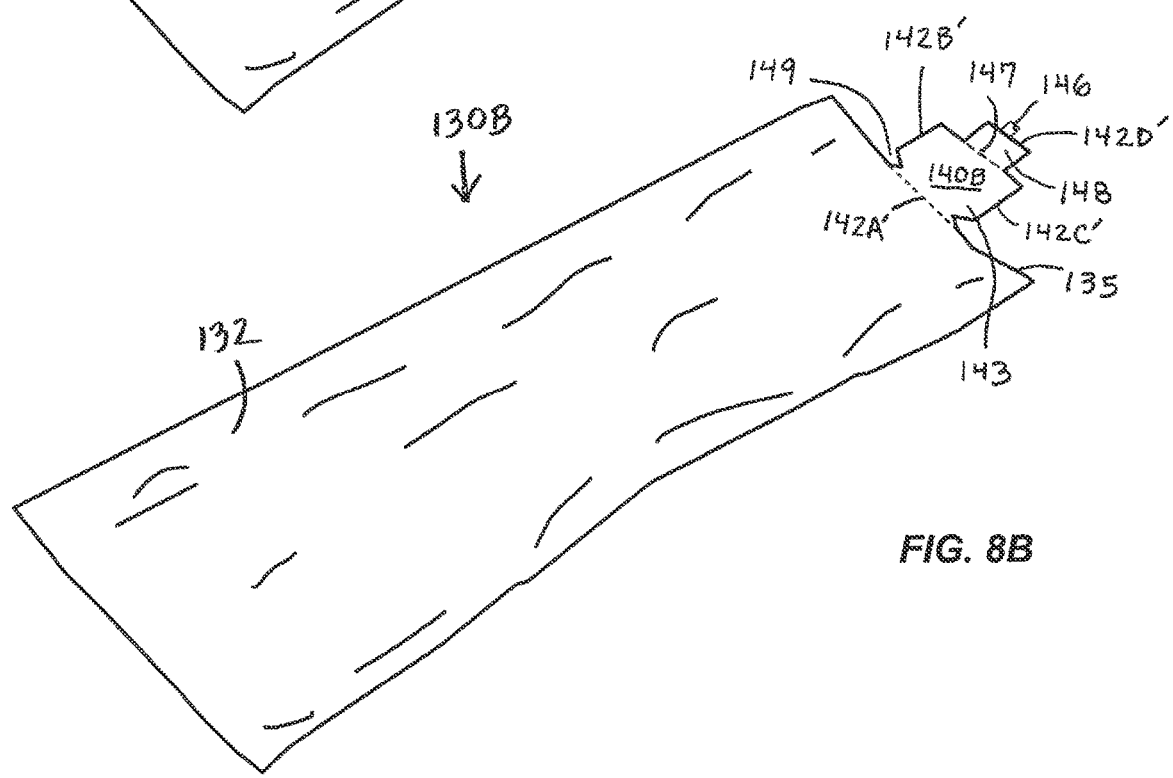
FIG. 8B is a bottom plan view of a surface covering member similar to that shown in FIG. 8A, but with the wrapper panel including a variable width, including a proximal portion having an increased width and a reduced width distal portion.

FIG. 8B is a bottom plan view of a surface covering member 130B similar to that shown in FIG. 8A, but with a wrapper panel 140B having a variable width, including a reduced width distal portion 148 that may be tucked (along intermediate fold line 147) into a pouch if (and when) the wrapper panel 140B is affixed along second and third edges 142B', 142C' to the pliable sheet material 132. The wrapper panel 140B is a continuous extension of the pliable sheet material 132. The wrapper panel 140B extends continuously from an end 135 of the pliable sheet material 132. The wrapper panel 140B includes peripheral edges 142A' to 142D', wherein a first peripheral edge 142A' is configured to form a fold (e.g., a single fold) with the pliable sheet material 132. Inset transition portions 149 are provided between the first peripheral edge 142A' and second and third peripheral edges 142B', 142C', wherein the inset portions 149 may aid in forming accordion folds along the second and third peripheral edges 142B', 142C', if desired. An inner surface 143 of the wrapper panel 140B is shown. The fourth peripheral edge 142D' of the wrapper panel 140B may be removably affixed to an inner surface of the pliable sheet material 132 with a closing member 146 that may include an adhesive surface or a portion of a hook-and-loop fastener. Optionally, when the wrapper panel 140B is folded upward along the first peripheral edge 142A', the second and third peripheral edges 142B', 142C' of the wrapper panel 140A may be removably or permanently affixed to the inner surface 143 of the pliable sheet material 122 to form a pouch into which the distal portion 148 may be tucked.

Figure 9:
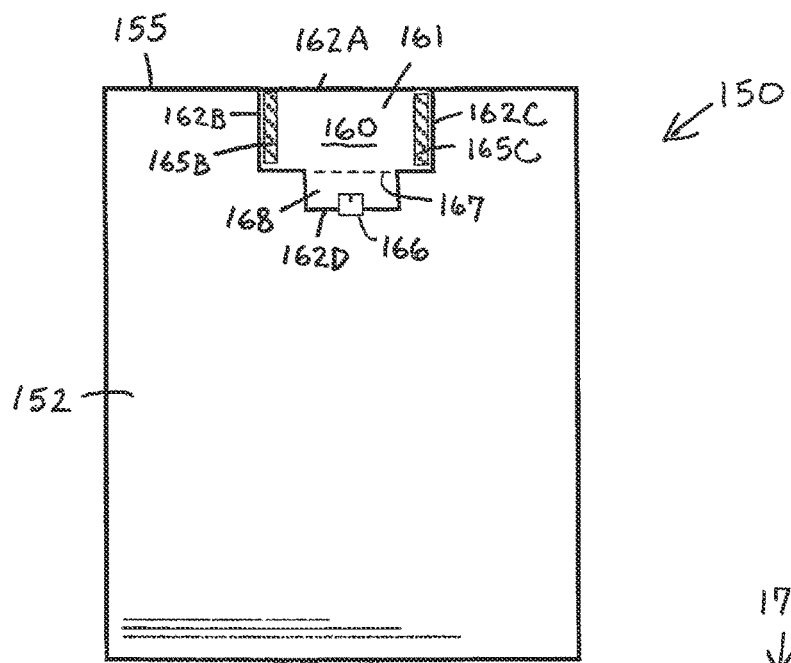
FIG. 9 is a bottom plan view of a generally rectangular surface covering member including a variable width wrapper panel as a continuous extension of a pliable sheet material, with the wrapper panel folded over a remainder of the pliable sheet material, the wrapper panel including lateral seams and a closing member arranged at one end thereof, according to one embodiment.

FIG. 9 is a bottom plan view of a generally rectangular surface covering member 152 including a variable width wrapper panel 160 as a continuous extension of a pliable sheet material 152 at an end 155 thereof, with the wrapper panel 160 folded over a remainder of the pliable sheet material 152. An outer surface 161 of the wrapper panel 160 is shown. The wrapper panel 160 includes first to fourth peripheral edges 162A-162D, with lateral seams 165B, 165C arranged along side peripheral edges 162B, 162C. A reduced width distal portion 168 of the wrapper panel 160 that may be tucked (along intermediate fold line 167, under which the distal portion 168 is not affixed to the pliable sheet material 152) into a pouch formed by the wrapper panel 160. The fourth peripheral edge 162D of the wrapper panel 160B may be removably affixed to an inner surface of the pliable sheet material 152 with a closing member 166 that may include an adhesive surface or a portion of a hook-and-loop fastener.

Figure 10:
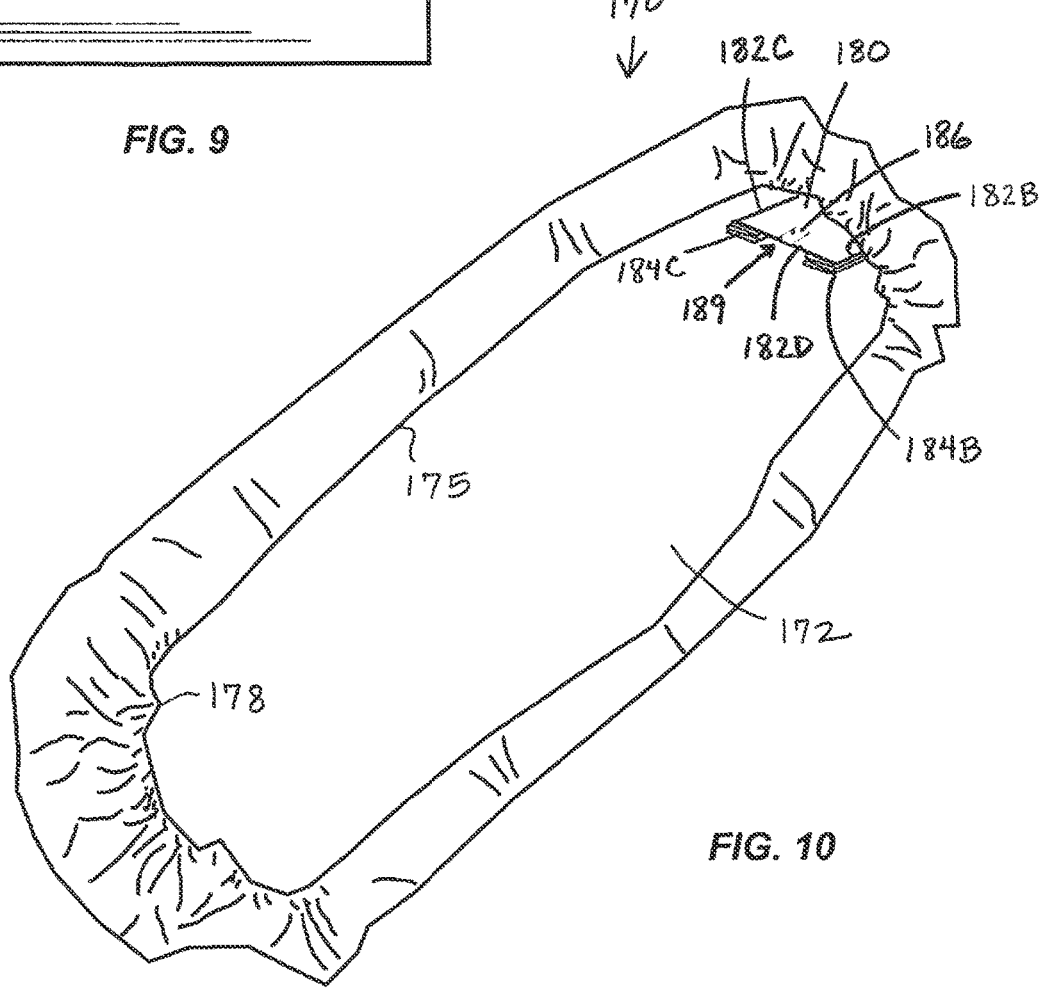
FIG. 10 is a bottom plan view of a fitted surface covering member including a wrapper panel having accordion folds along edges of the wrapper panel and forming a pouch.

FIG. 10 is a bottom plan view of a fitted surface covering member 170 including pliable sheet material 172 with a wrapper panel 180 having accordion folds 184B, 184C along side peripheral edges 182B, 182C thereof, with the wrapper panel 180 forming a pouch having a pouch opening 189. The pliable sheet material 172 includes at least one edge 175 with fitted regions 178 that may include elastic or other appropriate means to permit the surface covering member 170 to at least partially conform to an underling object to be covered. The fourth peripheral edge 182D of the wrapper panel 180 may be removably affixed to an inner surface of the pliable sheet material 172 with a closing member 186 that may include an adhesive surface or a portion of a hook-and-loop fastener.

Figure 11A:
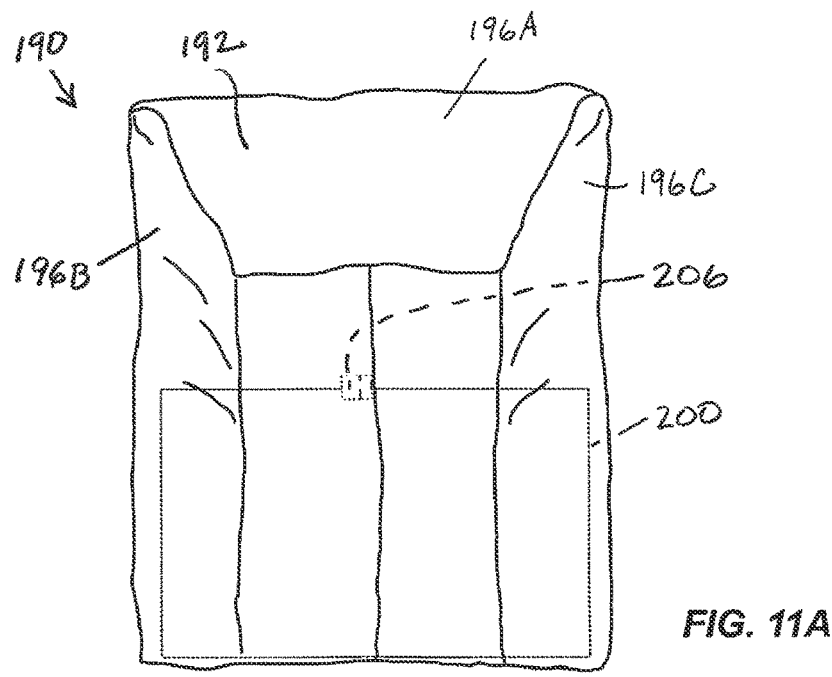
FIGS. 11A-11D show a surface covering member in various states of being compacted and inserted into a pouch formed by a wrapper panel having a closing member at one end of the wrapper panel.
Figure 11B:
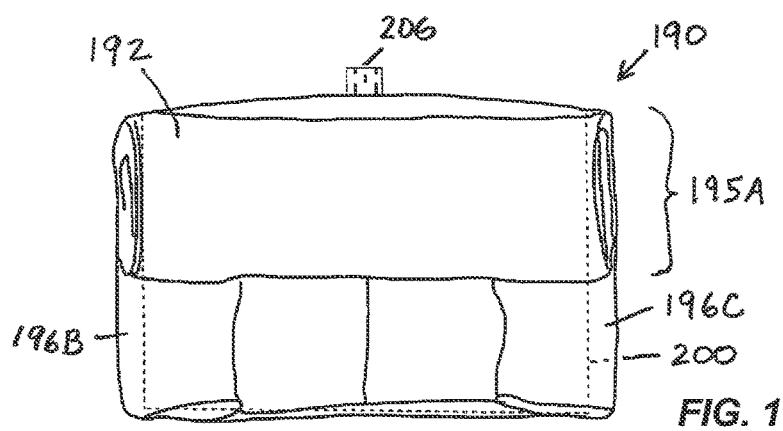
Figure 11C:
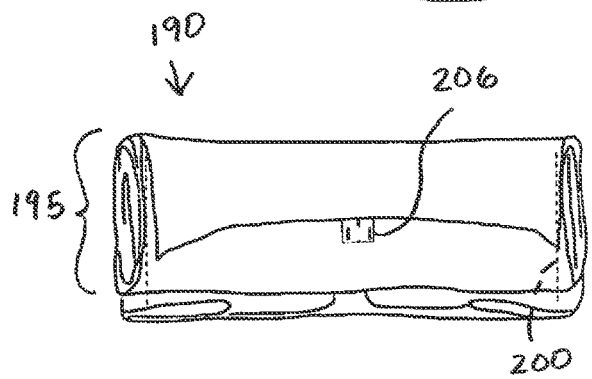
Figure 11D:
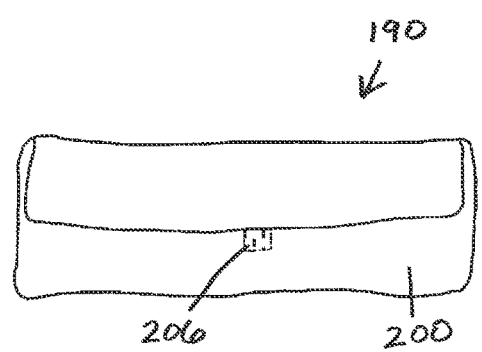

FIGS. 11A-11D show a surface covering member 190 in various states of being compacted and inserted into a pouch formed by a wrapper panel 200 having a closing member 206 at one end of the wrapper panel 200. In FIG. 11A, an end portion 196A and side portions 196B, 196C of a pliable sheet material 192 are folded inward. FIG. 11B shows the items of FIG. 11A after the end and side portions are partially compacted (by folding and rolling) to form a partial bundle 195A. FIG. 11C shows formation of a bundle 195 after compaction is completed. FIG. 11D shows the surface covering member 190 after the bundle 195 is inserted into (and enveloped by) a pouch formed by the wrapper panel 200, with the extended closing member 206 maintaining the compacted and bundled surface covering member in a state being enveloped by the pouch formed by the wrapper panel.

FIGS. 12A-12D show a surface covering member 210 in various states of being compacted (e.g., by folding and rolling) to be maintained in a compacted state with a (non-pouch) wrapper panel 220 having a closing member 226 at one end thereof. In FIG. 12A, an end portion 216A and side portions 216B, 216C of a pliable sheet material 212 are folded inward and partially rolled FIG. 12B shows the items of FIG. 12A after the end and side portions are further compacted (by folding and rolling) to form a bundle 215, with an inner surface 223 of the wrapper panel 220 being visible. FIG. 12C shows the bundle 215 partially enveloped by the wrapper panel 220. FIG. 12D shows the surface covering member 210 after the bundle 215 is nearly fully enveloped by the wrapper panel 220, with an outer surface of the wrapper panel 224 being visible.

Figure 13:
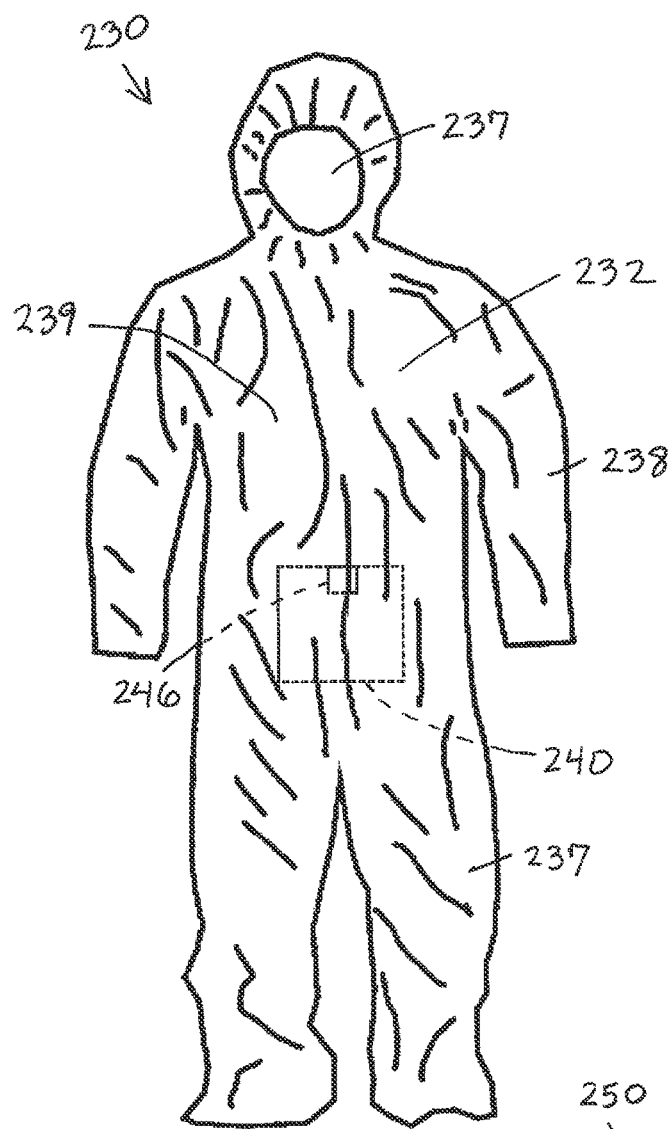
FIG. 13 is a front elevational view of a surface covering member embodied in a protective garment having a wrapper panel and closing member arranged along an interior surface of the surface covering member.

FIG. 13 is a front elevational view of a surface covering member 230 embodied in a protective garment formed of a pliable sheet material 232 with an affixed wrapper panel 240 and a closing member 246 arranged along an interior surface of the pliable sheet material 232. The protective garment 230 is configured to be worn by a human user and includes a hooded head opening 237, arm portions 238, a torso portion 239, and leg portions 237. After use (e.g., after exposure to biological or chemical contaminants), the surface covering member 230 may be removed by a user with eversion of the arm portions 238, torso portion 239, and leg portions 237, followed by compaction (e.g., by rolling, folding, and/or stuffing), and then inserted into the pouch formed by the wrapper panel 240 and maintained in a bundled state with the closing member 246.

Figure 14:
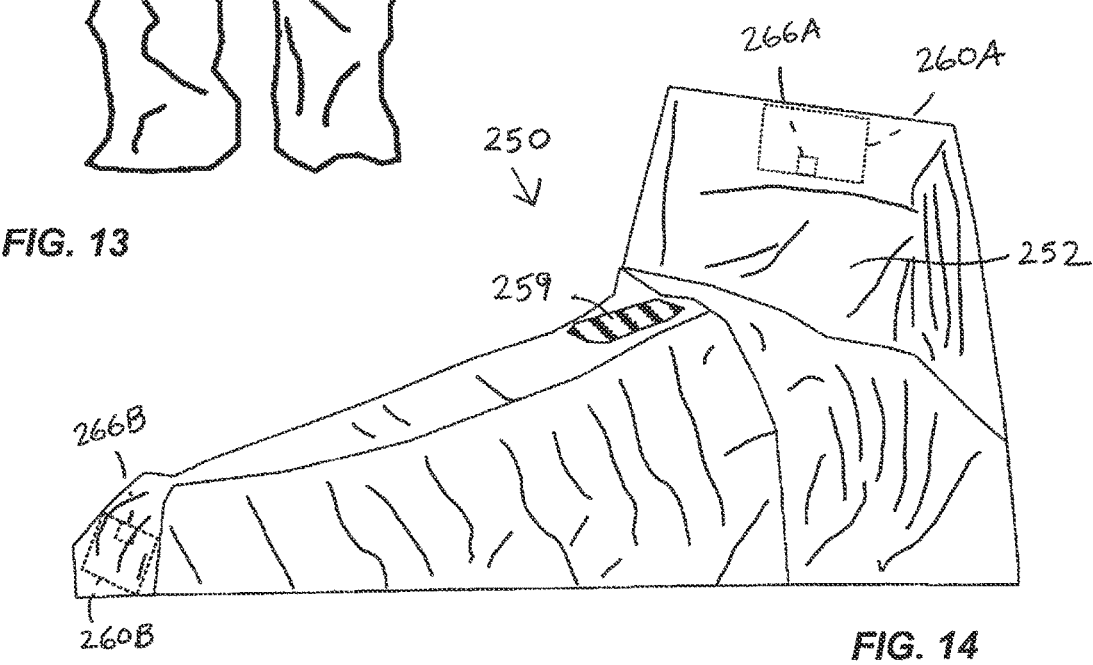
FIG. 14 is a perspective view of a surface covering member embodied in a surgical drape with a medial opening, the surface covering member having wrapper panels at two positions thereon.

FIG. 14 is a perspective view of a surface covering member 250 embodied in a surgical drape with a medial opening 259, the surface covering member 250 including a pliable sheet material 252 with wrapper panels 260A, 260B (and associated closing members 266A, 266B) at two positions along an inner surface of the pliable sheet material 252.

Figure 15A:
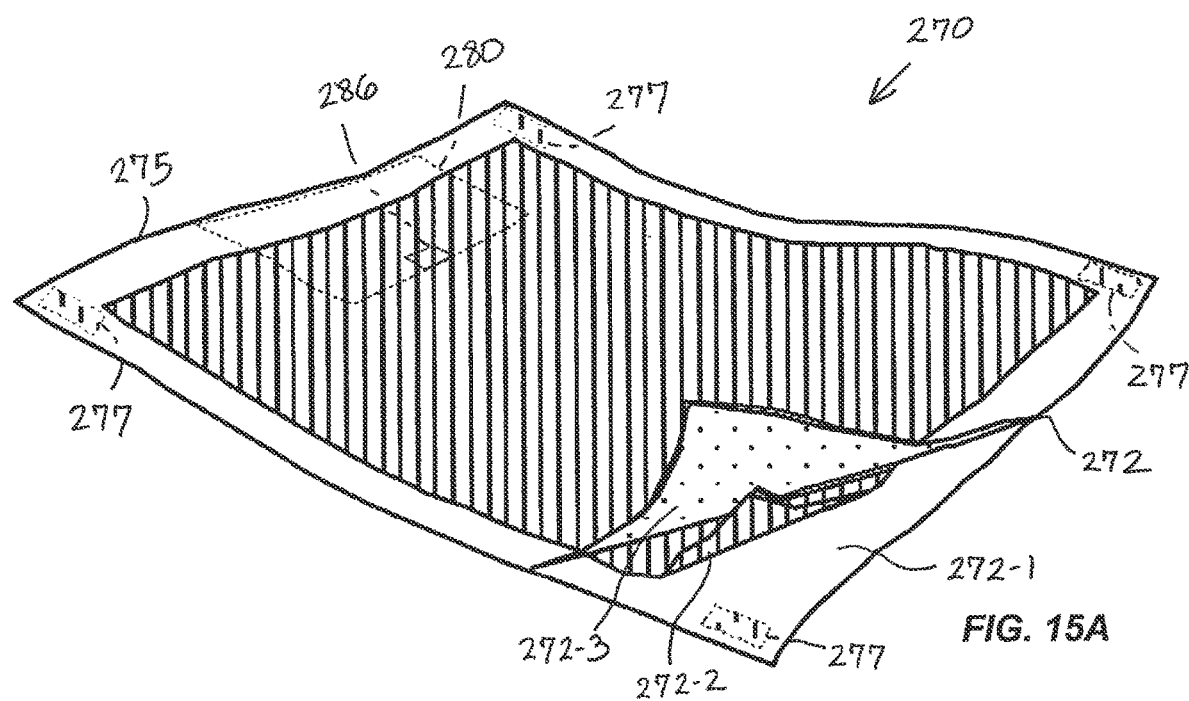
FIG. 15A is an upper perspective, partially exploded view of a surface covering member including an upper permeable layer, a middle absorbent layer, and a bottom liquid-penetration-resistant layer, showing a wrapper panel with a closing member and separate surface adhering elements along a lower surface of the surface covering member.

FIG. 15A is an upper perspective, partially exploded view of a surface covering member 270 including a pliable sheet material 272 composed of an upper permeable layer 272-3, a middle absorbent layer 272-2, and a bottom liquid-penetration-resistant layer 272-1. A wrapper panel 280 with a closing member 286, and separate surface adhering elements 277, are provided along a lower surface of the pliable sheet material 272. The surface covering member 270 may optionally be embodied in an absorbent mat or absorbent pad, optionally augmented with padding material (not shown) between the absorbent layer 272-2 and the liquid-penetration-resistant layer 272-1 (or below the liquid-penetration-resistant layer 272-1). The surface adhering elements 277 may include or embody one or more adhesive strips, to permit the surface covering member 270 to be adhered to an underlying surface (of an article such as floor, equipment, seat, etc.) to be covered by the surface covering member 270.

Figure 15B:
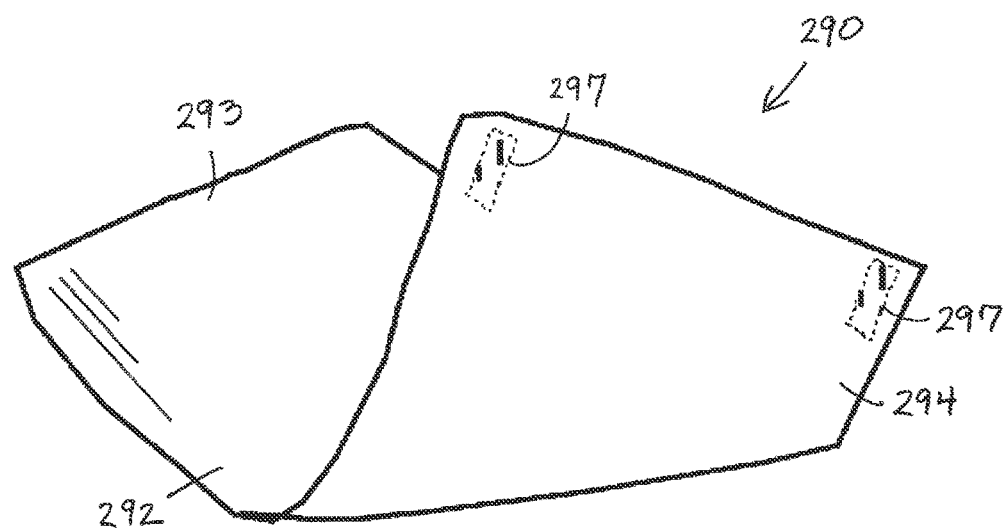
FIG. 15B is a lower perspective view of a surface covering member similar to that shown in FIG. 15A, showing surface adhering elements along the lower surface of the surface covering member.

FIG. 15B is a lower perspective view of a surface covering member 290 similar to that shown in FIG. 15A, showing surface adhering elements 297 along a lower (or inner) surface 294 of a pliable sheet material 292 of the surface covering member 290, with the lower surface 294 opposing an upper (or outer) surface 293 configured to be exposed to a surrounding environment. The surface covering member 290 may include some or all of the layers described in connection with the embodiment of FIG. 15A.

In addition to various surface covering members, the present disclosure relates to a method for compacting a surface covering member comprising a pliable sheet material and a wrapper panel, the pliable sheet material including at least one liquid-penetration-resistant layer. The method includes multiple steps. One step includes removing the surface covering member from a covered surface. Another step includes folding (and/or rolling) opposing first and second edges of the surface covering member inward, and rolling the surface covering member with folded first and second edges in a direction from one of a third or fourth edge to an other of the third or fourth edge to place the surface covering member into a compacted state. Another step includes opening at least one selectively deployable adhesive tab joined to a wrapper panel to disengage at least a portion of the wrapper panel from the surface covering member. Another step includes at least partially enveloping the compacted surface covering member with the wrapper panel. Yet another step includes deploying the at least one selectively deployable adhesive tab to maintain the compacted pliable sheet material in a state of being at least partially enveloped by the wrapper panel. In certain embodiments, the surface covering member is embodied in a wearable protective garment configured to be worn by a human user, and the removing of the surface covering member from the covered surface comprises removing the wearable protective garment from at least arms and a torso (optionally, additionally removing the wearable protective garment from a head and/or legs) of the human user. In certain embodiments, the surface covering member is embodied in a disposable healthcare drape, a disposable healthcare equipment cover, or a disposable equipment drape. In certain embodiments, the surface covering member is embodied in one of the following disposable items: a flat or fitted bedding cover, a flat or fitted stretcher cover, a blanket, a seating surface cover, a tarpaulin, an absorbent pad, or an absorbent mat.

Those skilled in the art will recognize improvements and modifications to the embodiments of the present disclosure. All such improvements and modifications are considered within the scope of the concepts disclosed herein and the claims that follow.

What is claimed is:

1. A medical covering member configured to be positioned on, above, or below a human, the medical covering member comprising:
    a pliable sheet material including at least one liquid-penetration-resistant layer extending across an entirety of the pliable sheet material and being characterized by a water impact resistance of no greater than 4.5 g when subjected to an American Association of Textile Chemists and Colorists 42 Impact Penetration test;
    a wrapper panel comprising a continuous extension of the pliable sheet material along a first peripheral edge of the wrapper panel, the wrapper panel having a width that is less than a width of the pliable sheet material; and
    at least one selectively deployable adhesive tab positioned on the wrapper panel;
    wherein the wrapper panel is configured to completely envelop the pliable sheet material when the pliable sheet material is compacted by one or more of rolling and folding, and the selectively deployable adhesive tab is configured to be deployed to maintain the compacted pliable sheet material in a state of being completely enveloped by the wrapper panel;
    wherein the medical covering member is embodied in one of the following items: a disposable healthcare drape, a disposable healthcare equipment cover, a disposable equipment drape, a disposable healthcare fitted bed sheet, a disposable fitted stretcher cover, a disposable healthcare flat bed sheet, a disposable flat stretcher cover, a disposable healthcare blanket, or a disposable absorbent mat.

2. The medical covering member of claim 1, wherein the selectively deployable adhesive tab is configured to affix a portion of the wrapper panel against a portion of the pliable sheet material when the surface covering member is in a non-compacted state.

3. The medical covering member of claim 1, wherein the wrapper panel is affixed to the pliable sheet material with one or more seams at second and third peripheral edges of the wrapper panel.

4. The medical covering member of claim 3, wherein the one or more seams comprise one or more of adhesive seams, heat-welded seams, ultrasonically-welded seams, or sewn seams.

5. The medical covering member of claim 3, wherein the wrapper panel forms a pouch having a pouch opening.

6. The medical covering member of claim 1, wherein the pliable sheet material comprises one or more adhesive strips on the pliable sheet material and configured to permit the surface covering member to be adhered to a surface to be covered by the surface covering member.

7. The medical covering member of claim 1, further comprising printed indicia on at least one of the wrapper panel and the pliable sheet, the printed indica including instructions for use of the surface covering member to assist a user in completely enveloping the pliable sheet material with the wrapper panel when the pliable sheet material is compacted by one or more of rolling and folding.

8. The medical covering member of claim 1, wherein at least a portion of the wrapper panel comprises at least one functional additive selected from the group consisting of antimicrobial agents and scented agents.

9. The medical covering member of claim 1, embodied in a disposable healthcare drape, a disposable healthcare equipment cover, or a disposable equipment drape.

10. The medical covering member of claim 1, embodied in a disposable healthcare fitted bed sheet, or a disposable fitted stretcher cover.

11. The medical covering member of claim 1, embodied in a disposable healthcare flat bed sheet, a disposable flat stretcher sheet, a disposable healthcare blanket, or a disposable absorbent mat.

12. The medical covering member of claim 1, wherein the pliable sheet material comprises at least one meltbonded, spunbonded, or spin-melt-spin (SMS) polymer layer.

13. A method for compacting a medical covering member configured to be positioned on, above, or below a human, the medical covering member comprising a pliable sheet material and a wrapper panel comprising at least one accordion fold along one or more peripheral edges of the wrapper panel, the pliable sheet material having an inner face, having an outer face, and including at least one liquid-penetration-resistant layer extending across an entirety of the pliable sheet material and being characterized by a water impact resistance of no greater than 4.5 g when subjected to an American Association of Textile Chemists and Colorists 42 Impact Penetration test, the method comprising with the medical covering member positioned with the wrapper panel between the inner face and a covered surface, removing the medical covering member from the covered surface;

folding and/or rolling opposing first and second edges of the medical covering member inward, and rolling the medical covering member with folded and/or rolled first and second edges in a direction from one of a third or a fourth edge to the other of the third or the fourth edge to place the medical covering member into a compacted state;

opening at least one selectively deployable adhesive tab joined to the wrapper panel to disengage at least a portion of the wrapper panel from the medical covering member and expand the at least one accordion fold;

at least partially enveloping the compacted medical covering member with the wrapper panel; and deploying the at least one selectively deployable adhesive tab to maintain the compacted pliable sheet material in a state of being at least partially enveloped by the wrapper panel;

wherein the medical covering member is embodied in one of the following items: a disposable healthcare drape, a disposable healthcare equipment cover, a disposable equipment drape, a disposable healthcare fitted bed sheet, a disposable fitted stretcher cover, a disposable healthcare flat bed sheet, a disposable flat stretcher cover, a disposable healthcare blanket, or a disposable absorbent mat.

14. The method of claim 13, wherein the wrapper panel comprises a continuous extension of the pliable sheet material along a first peripheral edge of the wrapper panel.

15. The method of claim 13, wherein the medical covering member is embodied in a disposable healthcare drape, a disposable healthcare equipment cover, or a disposable equipment drape.

16. The method of claim 13, wherein the medical covering member is embodied in a disposable healthcare fitted bed sheet, or a disposable fitted stretcher sheet.

17. The method of claim 13, wherein the medical covering member is embodied in a disposable healthcare flat bed sheet, a disposable flat stretcher sheet, a disposable healthcare blanket, or an absorbent mat.

18. The method of claim 13, wherein the pliable sheet material comprises at least one meltbonded, spunbonded, or spin-melt-spin (SMS) polymer layer.

* * * * *